United States Patent [19]
Hewitt et al.

[11] Patent Number: 5,841,530
[45] Date of Patent: *Nov. 24, 1998

[54] INDUSTRIAL VIEWING STATION FOR INSPECTION OF DEFECTS

[76] Inventors: Frederick G. Hewitt, 545 Chapel Ln., Eagan, Minn. 55121-2329; Steven J. Orfield, 5624 Edgewater Blvd., Minneapolis, Minn. 55417

[ * ] Notice: The term of this patent shall not extend beyond the expiration date of Pat. No. 5,686,987.

[21] Appl. No.: 936,638

[22] Filed: Sep. 24, 1997

Related U.S. Application Data

[63] Continuation of Ser. No. 580,760, Dec. 29, 1995, Pat. No. 5,686,987.

[51] Int. Cl.$^6$ .................................................. G01N 21/00
[52] U.S. Cl. .............................................................. 356/237
[58] Field of Search ..................................... 356/237, 239

[56] References Cited

U.S. PATENT DOCUMENTS

| | | |
|---|---|---|
| 2,867,149 | 1/1959 | Goddard . |
| 3,314,328 | 4/1967 | Boettcher . |
| 3,396,627 | 8/1968 | Rouy et al. . |
| 3,439,988 | 4/1969 | Breske . |
| 3,815,998 | 6/1974 | Tietze . |
| 4,062,623 | 12/1977 | Suzuki et al. . |
| 4,448,527 | 5/1984 | Milana . |
| 4,523,849 | 6/1985 | Stone . |
| 4,547,073 | 10/1985 | Kugimiya . |
| 4,863,268 | 9/1989 | Clarke et al. . |
| 4,895,448 | 1/1990 | Laird . |
| 4,907,888 | 3/1990 | Clarke et al. . |
| 4,920,385 | 4/1990 | Clarke et al. . |
| 4,929,846 | 5/1990 | Mansour . |
| 4,966,455 | 10/1990 | Avni et al. . |
| 5,041,726 | 8/1991 | Chang et al. . |
| 5,090,804 | 2/1992 | Wong et al. . |
| 5,125,741 | 6/1992 | Okada et al. . |
| 5,225,890 | 7/1993 | Lee et al. . |
| 5,331,169 | 7/1994 | Tanaka et al. . |
| 5,436,726 | 7/1995 | Ventura et al. .......................... 356/237 |

OTHER PUBLICATIONS

Orfield, *Lighting Design & Application*, "Photometry and Luminance Distribution: Conventional Photometry Versus CapCalc", (Jan. 1990), page numbers not available.
Orfield, *Sound & Communications*, "The Consultant' Own Office. Setting up the Workplace",37, (Jun. 1991).
Orfield, *LD+D*, "Visual Simulation: Prototyping Visual Performance vs. Lighting Products", 32–34, (Sep. 1992).
Orfield, *Sound & Communications*, "Data Projection and Visual Intelligibility: Part One — Background", 60–66 (no date available).
Orfield, *Sound & Communications*, "Data Projection and Visual Intelligibility: Part Two: Initial Findings", 57–64, (Oct. 1992).
Orfield, *LD+A*, "Visual Performance in Industrial Lighting Design", 11–14, (Dec. 1994).
Orfield et al., *Lighting Design + Application*, "Energy Efficiency via Asymmetric Office Lighting", 40–43 (Nov. 1987).
Orfield et al., *LD+A*, "Task–Specific for Low–Contrast Tasks", 35–38 (Jun. 1992).
Orfield et al., *LD+D*, "Traffic Court: Signals Undergo Trial by Jury", 33–36, (Jan. 1994).

*Primary Examiner*—Frank G. Font
*Assistant Examiner*—Amanda Merlino

[57] ABSTRACT

A method of establishing a lighting system and viewing environment for conduct of visual task is provided. The method generally includes steps of providing a visual performance lab, conducting a visual performance study, and constructing an industrial viewing station based upon the results of the visual performance study. The invention also concerns provision of a preferred visual performance lab and development of preferred industrial viewing stations.

21 Claims, 3 Drawing Sheets

INDUSTRIAL VIEWING STATION FOR INSPECTION OF DEFECTS

This is a Continuation of application Ser. No. 08/580,760, filed Dec. 29, 1995, U.S. Pat. No. 5,686,915 which application is incorporated herein by reference.

FIELD OF THE INVENTION

The present invention relates to visual task assessment and lighting and environment design. In particular, it concerns evaluating appropriate lighting and environment conditions for conduct of various tasks; and, equipment for conduct of the methods. It also concerns methods and apparatus for conducting visual performance studies, and for implementation of selected lighting designs and programs in the workplace to enhance performance.

BACKGROUND OF THE INVENTION

Visual performance essential to most industries. It is used, for example, for quality control purposes. In particular, in many industries viewers visually examine materials or manufactured items for defects or appropriate assembly and function. Such visual tasks may be heavily relied upon by the industries involved for maintenance of quality standards and products.

In general, industries have not developed methods of enhancing or optimizing conditions under which such visual tasks are performed. Indeed, in most industries little effort has been made to enhance the conditions under which visual tasks are performed.

In addition, there is a general desire to develop automated systems for replacement of visual inspection by humans. However, for such approaches to be generally successful, it will be necessary to develop methods to define more accurately parameters affecting visual inspection, so that these parameters can then be used to help define automated systems. it is an object of the present invention to facilitate inspection and viewing processes. This is conducted through the presentation of methods, equipment and environments, for definitions of conditions for preferred conduct of visual tasks, and implementation of preferred visual performance techniques. Many of the principles and techniques described may also be used to facilitate automated processes.

SUMMARY OF THE INVENTION

According to the present invention, a method of establishing a lighting system for conduct of a visual task is provided. The method generally includes steps of: providing a visual performance lab; conducting a visual performance study; and, constructing an industrial viewing station based on the conduct of the visual performance study. More specifically, a visual performance lab is provided which includes at least: a viewing station; an arrangement for selectively positioning an object to be viewed and manipulating an orientation and/or distance of the object relative to the viewing station; and, a selectively controlled lighting arrangement. In typical and preferred applications, the selectively controlled lighting arrangement will include at least: an intensity control for selectively modifying an intensity of task light illuminating the object to be viewed; and, a background luminance control for selectively controlling background luminance viewable from the viewing station. Herein the term "task light" is generally meant to refer to the light source which is dedicated to illuminating the task. For example, in some instances the task light would be a localized light source focused on the task, in others it can be an architecturally mounted light focused more generally on the area in which the task is to be performed or on the object to be viewed.

A variety of arrangements for selectively positioning an object to be viewed and manipulating an orientation of the object relative to the viewing station can be used. In general, the arrangement will be such that an object positioned thereon can be rotated or have its angular orientation selectively modified relative to the viewing station.

In general the step of conducting a visual performance study concerns positioning a viewer at the viewing station and selectively modifying each of selected viewing variables. For example, the variables might be the orientation of the object being viewed, the intensity of task light illuminating the object being viewed, the background luminance, masking light luminance, light color or light angle. The visual performance study is generally conducted to determine preferred values for the variables, for example preferred orientation, task light intensity and background luminance for viewing the object. Herein the term "preferred" in this context is meant to refer to the favored selected value of the observer(s) at the viewing station. The term "preferred" is not meant to necessarily refer to a specific mathematical optimum, but rather is intended to be a narrative preference indication. That is, if the viewer is a human, the preferred value is the value for a variable indicated by that person as preferred for his or her viewing of the task. In some instances, the "preferred" value may be a range of values. If the observer is an automated system, the "preferred value" is typically the value at which detection/differentiation is "best" performed by the system.

The step of constructing an industrial viewing station for the object, based upon the visual performance study, is generally conducted by creating a viewing station for viewing objects, and providing at the viewing station illumination of the task or task object by using equipment that can be controlled to implement the preferred values obtained by conducting the visual performance study. For example, if a preferred intensity of task light is identified in the visual performance study, the step of constructing the industrial viewing station would include a step of providing lighting equipment selectively adjustable to provide that intensity. Other variables such as background luminance, color, angle of illuminating task light, amount of masking light, etc. may be involved as well.

In some preferred arrangements, the construction or arrangement for selectively positioning the object to be viewed may be a goniometer. However, a wide variety of equipment generally may be utilized for this purpose.

In some instances, the visual performance study may generally be conducted by: serially positioning members of a selected population of viewers at the viewing station; and, determining each viewer's preferences with respect to lighting and positioning variables in the preferred lighting condition. The information can then be assimilated to develop preferred ranges of values for implementation in the industrial viewing station, in a preferred lighting condition. In typical studies, with respect to each variable, a viewer will likely be identified who is the "least visually capable" with respect to that variable. It will often be the case (with respect to implementing a preferred condition with respect to that variable in an industrial viewing station) that the preferred value selected will be that person's preference, as the "lowest common denominator" for the relevant population with respect to that particular variable. For example, suppose in the test population a range of preferred intensities is found. In general, what will be selected for implementation will be the intensity at which the least visually capable viewer (with respect to intensity) could adequately perform the task. This type of implementation will help ensure that the task can be appropriately performed by any of a variety of viewers, in the field.

Also according to the present invention a visual performance lab is provided. In general, the preferred visual performance lab includes appropriate equipment for conduct of the study described above.

In addition, according to the present invention various industrial viewing stations are provided. In general, these stations will include equipment appropriate to implement the preferred lighting conditions identified by the lab study. In some instances, it will be preferred to provide equipment that is selectively adjustable to implement more than one lighting condition for preferred viewing. Typically, a visual surround will be included, to block outside light from reaching the viewing station; and, the visual surround will include a luminous surface, such as a grid, directed toward objects to be viewed.

DETAILED DESCRIPTION OF THE INVENTION

I. Enhancement of Visual Task Performance—Generally

Figure 1:
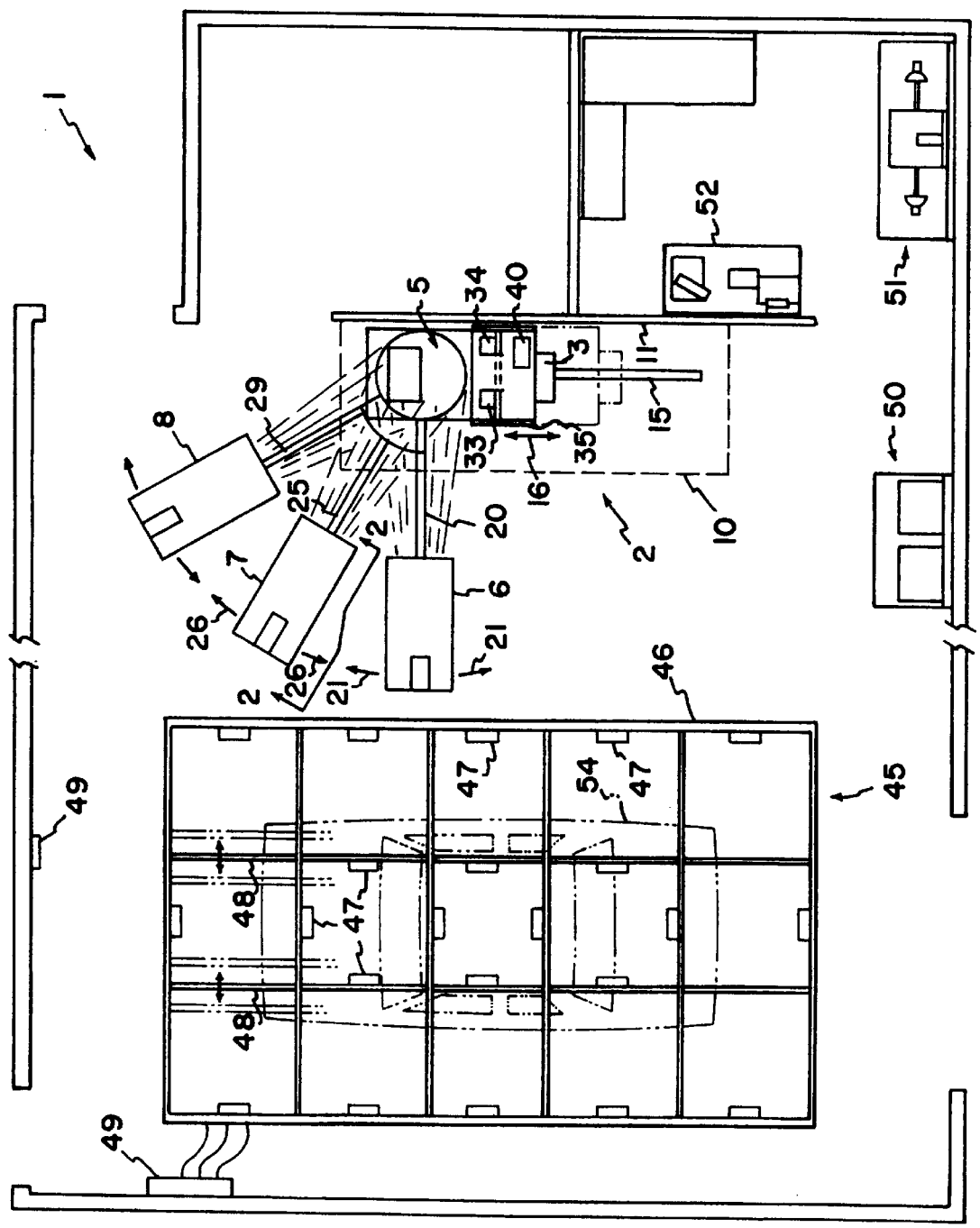
FIG. 1 is a fragmentary schematic representation of a visual performance lab according to the present invention.

Visual task performance is a problem in many work environments, both office and industrial. In general, the term "visual task" as used herein, is meant to refer to a task which is based upon some determination made visually. For example, a type of visual task could be a determination of whether to accept or reject a manufactured item, based upon visual examination (or inspection) for defects. A visual task under such circumstances would be the evaluation to be performed in order to determine whether a defect exists.

The conduct of visual task depends in part upon the ability of the viewer to "see" what needs to be examined, and to discern between acceptable and unacceptable conditions (or appropriate and inappropriate test performance). For example, if the visual task is an evaluation for defect, then it is important for the viewer(s) to be placed in an environment such that differences between items with the defects and items without the defects can be readily discerned. Variables with respect to this, disregarding selection of the particular viewer(s) for visual capabilities, at least include: physical positioning of the inspector(s) or viewer(s) relative to the item to be viewed; time allowed for the viewing process; type of light; amount of light; pattern of light; angle of light; and, background light, color and pattern. Other related variables will also be apparent from further descriptions herein. As will be apparent, with the techniques described herein it is feasible to evaluate the variables of greatest importance, finding preferred and in some instances optimum conditions for the viewer(s) This can be used to facilitate the viewing process.

An important component of certain applications of the techniques described herein is use of a systematic evaluation of visual task performance and lighting design. Such applications will generally avoid the pitfalls of less systematic, conventional techniques at enhancing visual performance. For example, the managers of many industrial facilities wherein a visual examination takes place may attempt to facilitate the examination by increasing the amount (intensity) of background (ambient) or specialized light in the portion of the facility where the examination takes place. It is often the case, however, that increasing the total amount of ambient light does not render the task of differentiating objects with defects from objects without defects any easier for the viewer(s). Indeed, in some instances, such an increase may make the visual task at hand, i.e. differentiation between objects with defects and objects without defects, more difficult to accomplish. Also, the increased glare typically associated with such increases in ambient lighting intensity may more readily weary the viewer(s), leading to substantial changes in the quality of the visual inspection throughout the day, depending upon the toll the glare takes on the viewer(s). Also, such increases in "power" or amount of lighting (i.e., intensity) may lead to significant added expense without enhancement in visual task performance.

Among the principles presented herein is a system for systematically evaluating visual task performance and enhancement or even optimization of that performance, through selected control of lighting variables. Although in some instances, as a result of applications and techniques described herein, it may be determined that preferred conditions or even optimization, for any given situation, would involve an increase in the overall amount (intensity) of light cast upon an object than had been used previously, the determination will have been made as a result of systematic evaluation and study, rather than chance. Thus, instances wherein the lights are "turned up" without any actual enhancement in the performance of the visual task will generally be avoided to advantage.

From the presentations herein, it will be understood that techniques according to the present invention may be utilized to enhance a very wide variety of operations. In some instances, specific examples are given in order to facilitate understanding of the general applicability of the techniques.

II. A Typical Application—Visual Inspection for Defects

The need for techniques and improvements according to the present disclosure can be in part understood by consideration of the some of the visual performance tasks which must be undertaken during the manufacture and assembly of products. Consider, for example, the exterior surfaces of products such as new cars and their manufacture.

The "newly finished" exterior surface of a vehicle can exhibit both structural defects and cosmetic defects. Herein the term "structural defects" in this and similar contexts is meant to refer to a defect that concern structural integrity, not merely cosmetic appearance. Herein the term "cosmetic defect" is meant, in this and similar contexts, to refer to a defect which may be unacceptable because of purchaser or end user preference, without regard to whether it illustrates or indicates a lack of structural integrity. Both types of defects can be of great significance to an industry. For example, with respect to cosmetic defects it is estimated that each of the big three automotive manufacturers in this country (Ford, Chrysler and GM) expends an extra $0.5–1.0 billion dollars per year as a result of failures to appropriately detect exterior cosmetic defects in newly manufactured vehicles. This is in part because while the cosmetic defects, if detected, can often be readily and inexpensively repaired at the factory, if the defect goes unnoticed until the vehicle is delivered into the field, the extent of repair can be substantially higher. As to structural defects, a failure to detect may result in an expensive product failure in use.

Cosmetic Defects

A very important threshold issue with respect to cosmetic defects is their identification. Cosmetic defects should generally only be of concern if they are of concern to the purchaser/end user of a product. For example, the mere fact that a manager of an industrial facility perceives a cosmetic variation in a material as a defect, does not mean that the "defect" will be perceived as such by purchasers/end users of the material or product involved. For efficiency, it is important that the "visual inspector" at the facility of concern be focused on identifying and inspecting for those perturbations which are likely to be perceived as defects by the purchaser/end user, rather than those which would be perceived as defects by other populations or under other circumstances.

A first step, then, in evaluating many visual evaluation systems, especially with respect to cosmetic defects, is a determination of the threshold condition (or perturbation) which would be perceived by the relevant population as a defect.

With respect to this, it is important to understand that the purchaser/end user may well inspect the material or item concerned under lighting conditions significantly different than those existing in the industry plant. For example, the conditions under which a consumer views a new car for surface flaws may differ from those under which it is viewed in the manufacturing plant. Cosmetic defects readily viewable by the end user in the field may not be viewable at all under typical industrial lighting environments. Similarly, cosmetic defects perceived in the industrial environment may not be viewable at all by the purchaser/end user in the field.

Having defined the threshold perturbation at which a variation is considered a cosmetic defect by the relevant population is not the end of the inquiry. For example, it is generally necessary and desirable to develop evaluation conditions for the industry, so that evaluation for that particular defect can be efficiently and effectively conducted. In some instances this may concern mimicking the environment in which the purchaser/end user will inspect the item, so that the defect can be detected. In typical applications, it will involve developing conditions for application in the manufacturing plant to enhance perception of the particular type of defect of concern, by the viewer(s). Regardless of the approach used, however, it will generally be preferred to develop conditions under which detection of the defect is facilitated and preferably is optimized for the visual capabilities of the viewer. That is, for the inspection process to be most effective, it is preferred that the conditions in the industrial (manufacturing) environment be developed to enhance the ability for the viewer involved to detect defects which, in general, are of the type or above the threshold that would be recognized by the purchaser/end user in the field as a defect. As will be apparent from descriptions below, in some instances this may involve developing viewing stations in the industry that can be "customized" for conditions of viewing, as the viewer is changed from shift to shift; and, in some instances, to accommodate changes in any given viewer's performance or performance capability, during a given shift or work day.

As indicated above, ultimately in many instances it is desirable to develop automated systems for the inspection. The parameters defined from studies such as those discussed herein can be used to develop and identify protocols for conduction of automated inspections. For example, using a visual performance study of the type discussed herein, one can determine a set of lighting conditions under which a defect is most readily visually perceived. One can then use automated equipment to view the defect under those conditions, and compare the detected image to images in which no defect is discernible. A comparison of the two can then be used to develop a threshold condition for the automated equipment to identify and recognize a defect. Video photometry equipment such as that described herein can in some instances be applied to facilitate this. It is anticipated that machine vision equipment will also be useable in performance of such evaluations. For example, cosmetic defects have in the past been a difficult task for machine vision, because the defects have a very complex definition and it has not been known how to light them. However, with the techniques defined herein, good lighting can be readily defined.

In general, defects in many materials such as the exterior surfaces of automobiles can be classified into one of two categories: dimensional defects; and, non-dimensional defects.

Dimensional defects are defects which result from some surface imperfection and have some dimensional component to them. For example, changes in a surface due to a ding, a dent, a bend or a scratch, are dimensional defects.

Non-dimensional defects are defects which do not necessarily result from a clear "macro" physical change in a surface plane or curve, but rather may be the result of differences or perturbations in surface texture, color, tone, finish, etc., i.e. changes at a much lower scale. These might, for example, be shifts in color due to lack of quality control in painting, etc. They may also be blemishes in patterns, etc.

Preferred techniques used to enhance detection of dimensional defects will often be different from preferred techniques used to enhance detection of non-dimensional defects. For example, dimensional defects in structural components are often detectable through utilization of techniques which result in shadowing of the defect. That is, the human eye can better detect a dimensional defect (or variance) in a surface if lighting conditions are selected such that the dimensional nature of the defect is enhanced through shadowing or similar effects. Thus, by angling the light at the surface relative to the viewer's point of view, shadows cast by the dimensional defect (or cast onto the dimensional defect) can be enhanced, facilitating identification of the defect. That is, shadowing is a technique which results in enhancement of contrast between the dimensional defect and its surrounding area. It can be used to give some indication of defect size. In general, the smaller the size of the defect, the more critical will be the angle of task illumination light to its detection. In other words, if the term "task illumination light" is used to refer to the light directed onto the object for facilitating examination to detect the defect, and if the defect is dimensional and its difference in size relative to surrounding areas is very small, it may be detectable only under very precisely controlled lighting conditions, with respect to the variables of: angle at which the task illuminating light is directed onto the object; intensity of the task illuminating light; and, position of the viewer relative to the object. The range of usable variations in each of these can become very limited, depending on the defect.

Many times approaches to the detection of dimensional defects concern utilizing light sources that are non-point sources. For example, they can be detected using fluorescent sources of light that do not emanate from a single point, but rather from a line or larger body (box). Such approaches, however, are generally less effective in identifying non-dimensional defects.

In general, non-dimensional defects (especially on high gloss surfaces) are more readily viewed or detected when point sources of light (such as incandescent lights, quartz-halogen lights or high intensity discharge (HID) lamps) are utilized for their identification. These general principles, then, can facilitate identification of preferred lighting conditions for detection of various types of defects. However, it is not meant by this to suggest that dimensional defects should never be evaluated utilizing point sources of light, nor is it suggested that non-dimensional defects should never be evaluated utilizing fluorescent light systems.

Preferred conditions for detection of non-dimensional defects will be affected by the nature of the surface being evaluated. For example, a very glossy (shiny or light reflecting) surface presents different problems for analysis than a less reflective, matte or stippled surface. With respect to automotive exteriors, generally very glossy or shiny finishes are involved. In general, using techniques according to the present invention, it has been found that with such surfaces the ability of the viewer to perceive defects is enhanced by examining the surface under conditions wherein an image or pattern is reflected onto the surface. Non-dimensional defects in a surface will be more readily perceived by the viewer under such circumstances, in part because they will be viewed as a variation in the reflected image. It is noted that such conditions, to a great extent, are analogous to the conditions under which the end user/purchaser also evaluates for defects in the field. For example, many car owners inspect the surface finish of their vehicles by examining a reflection of the environment in the shiny or glossy finish, although typically they use this technique to evaluate for dimensional defects, rather than merely non-dimensional defects.

In general, techniques of viewing reflected scenes in a finish in order to detect cosmetic defects will be referred to herein as "border interference" techniques.

In general, border interference techniques are inappropriate if the surface to be inspected is not highly glossy. Under such circumstances, generally optimizing lighting selection and angle will be the appropriate approach.

From the above discussions, it will be apparent that certain lighting variables are of great concern with respect to the development of appropriate lighting conditions for inspection. These are: nature of the light source (for example, point source or non-point source, fluorescent, incandescent, etc.), angle of light, and utilization of reflected patterns or images to facilitate detection. Other variables, however, may also be of great concern.

For example, intensity of the light to be directly applied to the object to be evaluated can significantly affect the ability of the viewer to detect the image. In many instances, intensity substantially greater than that at which optimum detection occurs may reduce the viewer's ability to see the defect or, in time, will generate sufficient stress and strain on the viewer's eye that performance is lowered. Indeed, it is now being recognized, as a result of studies involving techniques described herein, that in many instances much of the light cast upon an object during inspection is not only in excess of that needed for an efficient inspection, and thus is wasteful with respect to energy, but it also results in a reduction of performance, i.e. less than optimal evaluation for the defect.

Other light (background light or masking light for example) in the viewing area involved may also be of concern. That is, light which is within the viewer's field of vision, or which spills onto the object being viewed and which is not directly cast upon the project or surface being evaluated or which is not presented in a form optimized for the viewing task, may effect the inspector's ability to detect the defects.

The term "masking light" herein is used to refer to light which is cast upon an object being viewed but which is not primarily dedicated to the task; i.e. which is not task illuminating light. Such light is generated from other sources in the room (windows, other lights, etc.) and its effect may be to in part mask the optimum affects of the lighting condition selected from the task illuminating light. Control of such masking light, or developing conditions under which the masking light is accounted for, will be important in some instances, to facilitate the viewing process. The term "background light" herein is meant to refer to a light source which is within the viewer's range of view, during the operation, but which is not the task illuminating source. Glare from such sources may also interfere with the viewer's ability to perceive the task.

Structural Defects

In general, evaluation of structural defects is subject to the same parameters and variables discussed above with respect to the detection of cosmetic defects. One significant difference is that, in general, the issue with respect to structural defects does not concern whether or not the end user/purchaser would perceive the perturbation and identify it as a defect. Rather, the defect would typically be identified by the design or performance engineers, based upon performance testing and evaluation. The visual task, then, is in the detection of the image which represents identification of an item possessing the structural defect. Such studies would typically not involve a phase in which a threshold evaluation is made of end user/purchaser identification of the presence of the defect. Rather, products possessing the threshold defect would typically be identified by the manufacturer/producer or by some testing process, and then those products would be utilized for studies according to the present invention to identify preferred or optimum conditions for visual evaluation. This will be more apparent from descriptions below.

In general, structural defects will typically be detected by visual evaluation for either a corresponding dimensional or non-dimensional defect in the object. Thus, the "problem" concerns enhancement of conditions for detecting either dimensional or non-dimensional defects, depending on which one or ones are involved. The principles discussed above with respect to viewing of cosmetic defects will, in general, be applicable to evaluations for structural defects.

III. Equipment, Facilities and Procedures for Identifying Conditions of Inspection

A. Variables

In general, identification of a defect requires an individual (inspector) to make a conceptual response to a visual image of an object. Thus, the object must be detected, recognized and scaled. The lighting conditions should be such that the visibility of the defect is enhanced.

Visibility depends on such image characteristics and variables as:

1. Target luminance;
2. Background luminance;
3. Luminance contrast;

4. Color;
5. Color contrast;
6. Object size;
7. Object shape;
8. Image complexity;
9. Background adaptation;
10. Veiling glare;
11. Disability glare;
12. Age factors;
13. Visual disabilities.
14. Viewing speed.

These variables/parameters can be divided into several groups: those which primarily concern the lighting conditions under which the viewing is conducted; those which primarily concern the nature or characteristics of the item being viewed; and, those which primarily concern the capability of the one(s) conducting the inspection.

As to those which concern the abilities of the person(s) doing the viewing, generally factor 12 (age factors) and 13 (visual disabilities) are of greatest concern. In general, visual capabilities and other visual performance attributes diminish with age. In some instances, the efficiency of visual evaluation tasks can be enhanced simply by selecting viewers from a population pool having greater visual acuity. This may not always be a practical solution, however. It is noted, for example, that in many industries visual task viewers are older, longer term employees who are no longer well suited for more physically demanding tasks. Compensation for visual disabilities, eyeglass, etc. may be possible in some applications, but inappropriate in practice in others.

The viewing speed (number 14) in part concerns the ability of the viewer to adjust to changes in lighting conditions, in order to perceive a defect. For example, if an object is moving along an assembly line, under a reflected light pattern, it will be important to select a condition under which the viewer is provided with sufficient time to receive and assess the image, to perceive whether the defect is present. Similarly, if lighting conditions are being changed while viewing a stationary object, a sufficient time to allow the viewer's eyes to adjust to the changing conditions may be necessary to facilitate the viewing process.

Factors which concern the nature of the object being evaluated greatly concern items 6 and 7 (size and shape). These variables are not as subject to modification to facilitate the inspection process. However, lighting conditions can be particularly selected to facilitate inspection depending on the size or shape of the object being evaluated.

In general, by the terms used in the table above, the following is meant:

"Color". Color is that aspect of visual perception by which an observe may distinguish differences between two structure-free fields of view of the same size and shape, such as may be caused by differences in the spectral composition of the radiant energy concerned in the observation. In this sense, the term color is sometimes referred to as "perceived color" to distinguish it from color used in the sense of "psychological color".

"Target luminance". Target luminance is the average luminance of an object of interest for detection or identification.

"Luminance". The quotient of the luminous flux at an element of the surface surrounding the point, and propagating in directions defined by an elementary cone containing the given direction, by the product of the solid angle of the cone and the area of the orthogonal projection of the element of the surface on a plane perpendicular to the given direction.

"Background luminance". The average luminance of the immediate background surrounding a target or object of interest.

"Luminance contrast". The relationship between the luminance of an object (target) and the luminance of the immediate background. It is equal to the difference between the luminance of the background and the object divided by the luminance of the background.

"Color contrast". The difference in chromaticity between two colors. Measured in units of chromaticity difference threshold or the difference on a uniform color space.

"Object size". The solid angle subtended by an object from the point of observation.

"Object shape". The geometric contour of the object projected onto a plane perpendicular to the direction of observation.

"Image complexity". The quantity of detail in an image in terms of kinds of boundaries between areas of different luminance, color, texture, etc.

"Transient adaptation". The process by which the retina becomes accustomed to more or less light than it was exposed to during an immediately preceding period. It results in a change in sensitivity to light.

"Background adaptation". Refers to the final state of the adaptation process, as in "reaching a condition of adaptation to a specific luminance level".

"Veiling glare". Regular reflections that are superimposed upon diffuse reflections from an object and that partially or totally obscure the details to see by reducing contrast. Also, the regular reflections that are superimposed on an image or object that transmitted through a transparent medium such as a glass plate.

"Age factors". General deterioration of visual capabilities with age, such as: reduced visual acuity, reduced accommodation (focus range), decreased transmission of the cornea, increased scattering centers in the vitreous humor, decreased transmission of the lens, etc.

"Visual disabilities". Clouding of the cornea, damage to retina, color blindedness, etc.

"Point source". A source of radiation the dimensions of which are small enough, compared with the distance between the source and the irradiated surface, for them to be neglected in calculations and measurements.

"Line source". A source of radiation in shape of a line in which the width is small in comparison to the length and the width has a dimension of a point source with respect to the irradiated surface and the length does not.

"Area source". A source of radiation in which the dimensions are greater than point source dimensions.

"Luminance distribution". The variation in spectrum or color over the surface of a luminance source.

"Directional distribution". The variation in directional characteristics over the surface of a luminance source.

"Polarization (polarized light)". Radiation whose electromagnetic field, which is transverse to the direction of propagation, is oriented in defined directions. The polarization can be rectilinear, elliptic, or circular.

"Disability glare". The effect of strong light in the eye whereby visibility and visual performance are reduced.

"Discomfort glare". Glare producing discomfort. It does not necessarily interfere with visual performance or visibility.

"Reflection (regular or specular)". That process by which incident light is redirected such that the angle of reflection is equal to the angle of incidence and both are in a plane which contains the normal or direction perpendicular to the surface.

"Scattering (diffuse reflection)". The process by which incident light is redirected over a range of angles.

"Transmission". A general term for the process by which light leaves a surface or medium on a side other than the incident side, without change in frequency.

"Absorption". A general term for the process by which incident light is converted to another form of energy, usually and ultimately to heat.

"Fluorescence". The emission of light (luminescence) as the result of, and only during, the absorption of radiation of shorter wavelength.

"Divergence (beam spread)". The angle between two directions in the plane in which the intensity is equal to a stated percentage of the maximum beam intensity.

The visual image of an object is contained in a complex visual scene which is a product of: the surface characteristics of objects in the scene; the environment; and, the light sources both in the scene as background and illuminating those objects in the visual scene. The light source characteristics that influence the details of the visual scene include:

1. Size, shape (example: point source, light source, area source, etc.).
2. Luminance distribution.
3. Spectral distribution.
4. Directional distribution (for example, spot or flood).
5. Polarization.
6. Temporal variations (for example, by flashing).
7. Coherence (for example, lasers).

The object surface characteristics that influence the details of the visual scene include:

1. Reflection.
2. Scattering.
3. Transmission.
4. Absorption.
5. Polarization.
6. Fluorescence.

Most of these characteristics are dependent on wavelength, polarization, angles of incidence and direction.

B. Methods of Analysis

In general, a process for developing a lighting environment system for improving or enhancing visual task performance comprises conduct of the following general steps or processes:

1. Definition of the task.
2. Development of laboratory test conditions.
3. Determination of task performance thresholds.
4. Lighting/performance investigations.
5. Specification of lighting characteristics for the task steps.
6. Design of task lighting environment system for industrial application.

In the instance of evaluations for cosmetic defects, in part the task may involve a study of an appropriate population to determine the threshold condition or variance recognized as a defect. Once such a study is conducted and the threshold conditions which comprise defects are identified, further studies can be conducted in order to enhance identification of those defects, in the industrial environment.

Alternatively, in many instances the defect may be defined within the industry itself, not by the end user/purchaser. These would include, for example, structural defects. In such instances, the task generally concerns collection of samples which exhibit structural defects and viewing of the samples under various test conditions, to determine optimal conditions or preferred conditions for recognizing and identifying the defects.

Identification of Defect Items, for Testing

A preliminary determination needed in studies according to the present invention will be identification of defect or defect conditions for the visual task. These can be collected from a variety of sources. For example, descriptions of defects can be assimilated from consumer defect complaints. Samples of the various defect or defect types, then, can be collected from returned items, etc. In addition, manufacturers can purposefully create defect items for use. Other companies may just collect defect items from an assembly line.

Visual Performance Lab

An important part of the process is the development of laboratory test conditions for the necessary evaluations. A principal goal in developing the laboratory environment is the development of test systems that will allow one variable to be changed in a controlled or measured manner while other variables are held constant or at fixed positions. It is desirable, however, to allow controlled variation in each of the variables, so that a systematic overall assessment and evaluation can be made. Herein, the term "visual performance lab" will be used to refer to a test environment for evaluating visual task performance.

A typical and preferred test environment for evaluations conducted in processes according to the present invention, at this stage, is the utilization of a visual performance lab with at least the following properties:

1. Each viewer (inspector) is positioned in the same spot for viewing during testing.
2. The object being viewed is positioned upon equipment, so that its position in space can be selectively modified. Typically, a goniometer will be used. A goniometer is a piece of equipment which can be adjusted to selectively rotate an object around three perpendicular axes, relative to a stationary observer.
3. Lighting intensity (or angle) directed onto the object positioned can be controlled.
4. Background lighting can be varied.
5. Background color/pattern can be varied.
6. In some instances, type of light can be varied.
7. In some instances, color of light can be varied.
8. In some instances, masking light can be varied.

Such laboratories conditions can be readily developed and constructed. An example is illustrated in the schematic of FIG. 1.

Referring to FIG. 1, reference numeral 1 generally indicates a visual performance lab according to the present invention. The lab 1 includes a visual performance test system 2. The test system 2 includes an observation or viewing station 3, task positioning equipment 5, and lighting equipment 6, 7, and 8. The system includes other lighting arrangements, described below.

The region enclosed by phantom line 10 and wall 11 is generally referred to herein as the "illuminated surround", and is the region which in typical operation will be enclosed by a blanket system or other enclosure arrangement. This can be used to control or prohibit exterior light from reaching the system 2. Alternatively, or in addition, the material enclosing in the illuminated surround may be selected in order to provide a background which can be illuminated at different levels to provide different levels of adaptation luminance for the subject.

The observation station 3 is the position whereat an observer would be placed during performance of a visual performance analysis using the test system. In the alternative, it is the location whereat sensing equipment of photometry equipment or similar apparatus would be positioned, during performance of a test using an automated detection system. In the arrangement shown in FIG. 1, the observation station (or carriage) 3 is positioned on track 15. Thus, it can be moved toward or away from the task position equipment 5 in the general directions indicated by double-headed arrow 16.

The task position equipment 5 is generally of mechanical construction in which a "task" or object to be examined is positioned for performance of the study. The equipment should generally be constructed to securely hold the task or object, while it is selectively manipulated or oriented in space for viewing by the observer. A goniometer may be utilized as the task positioning equipment. In general all that is required for the task positioning equipment 5 is that is can support the task or object and be controlled to position the task or object through whatever rotations or orientations are desired during a visual performance test. Thus, in some instances or applications movements around only one axis or two axes may be sufficient for appropriate study. Indeed, in some instances no rotational movement may be appropriate.

In general, in many instances an object of a visual performance test is to allow evaluation from the observation station, of the task or object, under circumstances which allow for all degrees of freedom; that is, observation of the object under each possible combination of selected lighting conditions or effects. For the particular arrangement shown in FIG. 1, this is facilitated by principal light sources (task light sources) 6, 7 and 8. In particular, source 6 is positioned on arm 20, which can be rotated horizontally along the arc indicated by arrows 21. Thus, the angle of the light emanating from source 6 and directed toward task performance equipment 5, relative to an observer at station 3, can be selectively modified by controlling the direction of arm 20.

Referring to lighting source 7, mounted on arm 25, preferably the direction of arm 25 is also selectively controllable for rotation in the direction of arrows 26. Also, preferably, light source 7 is mounted on arm 25 such that it can be adjusted vertically with respect thereto. A variety of mechanical arrangements, such as scissors jack 27, FIG. 2, can be used for this. Also, preferably, light source 8 can be adjusted by adjustment in the position of arm 29 and also vertically adjusted. In this manner, lighting sources 6, 7 and 8 can be controlled to allow for a wide variety of orientations with regard to the sample. It will be understood that additional lighting sources could also be utilized.

Still referring to FIG. 1, at 33 and 34 lights are positioned. These lights can be used to simulate masking light or background light, i.e. light spilling onto the observed sample that is not the direct task lighting. In the particular arrangement shown, lights 33 and 34 are positioned on the assembly 35 which moves along track 15, with observation station 3. Alternative arrangements, however, are usable.

The particular lighting equipment utilized for light sources 6, 7 and 8 will depend in part upon the study. For example, point sources of light could be used or linear sources (fluorescent tubes, for example) could be used. In addition, area sources, for example box lights, could be used. In addition, sources 6, 7 and 8 could be more exotic sources of light, such as video monitors, which could be used to generate a variety of images, patterns and luminance levels.

In a typical study one might use, for example, source 6 to provide the specific task light, i.e. the light shone onto the object for performance of the visual task by the observer, with sources such as 7 and 8 adjusted to cause (or mimic) background glare or other illumination sources. In general, at 40 control equipment is positioned for the observer at station 3 to adjust such parameters as lighting intensity, object orientation, light angle, light color, position along track 15, etc. That is, in general when human observers use station 3, the observer is provided with sufficient control over the variables of the system to be able to identify relative or local optimum for observation detection.

Still referring to FIG. 1, other equipment/facilities that might be utilized in a visual performance lab are illustrated. For example, at 45 a prototyping system is depicted. This arrangement may be, for example, a frame 46 at which various lights 47 can be positioned, to simulate an actual lighting station, for example an inspection system that would be installed in some industrial facility. For the arrangement 45 depicted, rack or frame 46 includes moveable supports 48, so that movement of lights positioned thereon is facilitated. In general, computer equipment, for example as illustrated at 49, can be used to control the various lights or banks of lights 47, in selected, preferred manners.

At 50, a video photometer computer system is shown. Video photometer systems are described, in general, below.

At 51, reflectance and gloss measurement equipment is depicted. This equipment can be used to measure differences in reflectance or gloss, which will provide information on the relative visibility of samples. That is, a sample will be placed in the reflectance and gloss measurement equipment, and the measurements taken can be compared to other samples. This will facilitate an assessment of the performance task, and correlation of various performance parameters with gloss or reflectance.

At 52, equipment for measuring the size of dimensional defects is provided. This can be used, for example, to correlate the size of a dimensional defect with the angle of light needed to facilitate detection of that defect.

Of course, a visual performance lab may be constructed with a variety of additional equipment to facilitate operations conducted therein. For example, various photosensor and photometric measuring system may be positioned as desired. Computer equipment can be utilized for automated control or automatic data collection. Mechanical arrangements which allow for automated movement of components or equipment may be desirable. A wide variety of types of equipment can be used in construction of the visual performance lab. The following examples are illustrative only. For directional lighting sources, equipment from Presco Lite of California, Omega of California, and Lightolier could be used. For asymmetric distribution lights (i.e. arrangements which distribute lights evenly along a plane), equipment from Elliptapar of New Haven, Conn., or Cramer Lighting of New York City can be used. If fluorescent lights are to be used, common sources include Columbia of Washington state and Daybrite of Tuppmo, Miss. can be used. Lighting control systems are available from companies such as Sterner Lighting of Winstead, Minn. or Lutron Corporation of Los Angeles, Calif. Grid systems are commonly available from local industrial supply houses, and they are readily adaptable for use in grids according to the present invention. Sample positioning systems will typically be custom built by a specialty fabricator. A proflicorder is available from Sheffield of Bendix Co., Dayton, Ohio. Video photometers are available from the National Research Council of Canada, in Ottawa.

In the particular prototyping system 45 depicted in FIG. 1, an automobile 54 is depicted in phantom. This is simply to indicate that the prototyping system could be used to allow modeling of an evaluation station for the exterior surface of a vehicle. Of course, prototyping systems could be constructed or designed for a variety of alternative tasks in addition.

Figure 2:
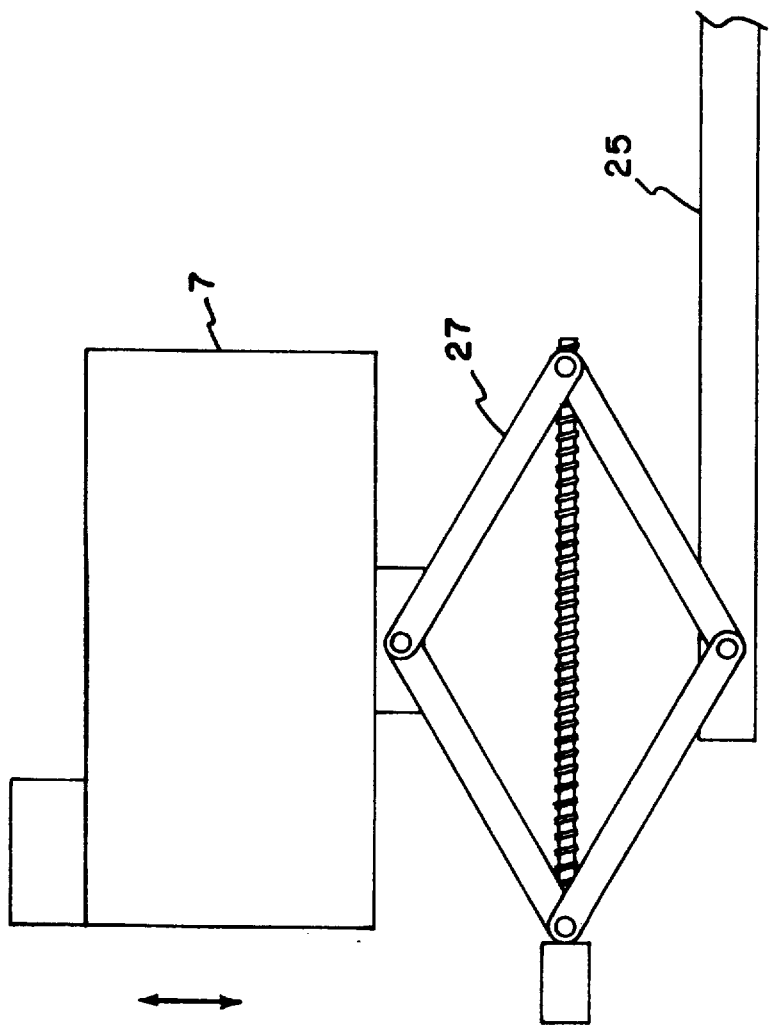
FIG. 2 is a fragmentary schematic side elevational view of a portion of the lab shown in FIG. 1, taken from the viewpoint of line 2—2 therein.

The system described with respect to FIGS. 1 and 2 is meant only as an example. In this section, general characteristics of visual performance lab, regardless of its specific construction, are discussed. In general, the preferred visual performance lab or test installation includes the following elements. At the center of the test installation is a three axis task holder. The task can be rotated about a vertical axis, a horizontal axis, and can be rotated about an axis through the center of the task and perpendicular to the vertical and horizontal axes. This allows the task to be oriented in all possible directions. The three axis sample holder is preferably designed so that both transparent or translucent samples can be investigated for light transmission situations. The task holder is also provided with capability of rapid sample change for quick and accurate task comparison testing. The viewing station or booth is located horizontally from the task holder and is arranged so that the viewer's eyes are at the same horizontal level as the center of the task holder. The direction of the viewing booth is fixed but the distance from the task holder can be changed.

The next element is a light source platform that rotates horizontally about a vertical axis through the center of the task holder. The platform holds the center of the light source at the horizontal level of the center of the task holder. This platform can be used for any number of different light sources. Changing light sources allows for control of lighting parameters such as size, luminance distribution, directional distribution, spectral distribution, color and polarization. Some of the readily available light sources are point sources such as incandescent light bulb, line sources such as fluorescent tube light bulbs, or area sources such as a light box or video monitor. This platform also provides for rotation about the axis from the light source to the task to change the orientation of the surface luminance distribution for sources that are not circularly symmetrical. One flexible light source that can be used is a video monitor or other flat screen source. This allows for a very wide range of both simple and complex luminance source distributions. An added advantage is the capability to rapidly change the light source characteristics for making quick and accurate visual comparisons.

A next element is a platform that rotates in the same manner as the previous platform. However, this platform does not rotate independently but is coupled to the task holder so that it rotates at twice the horizontal angle as the task holder. The next elements are several platforms to hold additional lights. These platforms rotate horizontally about the task holder like the first light source platform. In addition, they also rotate vertically about a horizontal axis through the center of the task holder. A next element is a visual surround that encloses the test installation so the background luminance can be controlled.

The viewing booth is designed so that the position of the viewer's eyes is fixed and repeatable. The viewing booth contains controls for changing the position and orientation of the elements (task and light sources) of the test installation. An additional set of controls is provided for an experimenter to control the test installation. Inputs can be controlled either to achieve a desired visual effect and positions and levels recorded, or to specify positions and levels and record visual parameters. In both cases the inputs and outputs can be monitored and controlled by computer.

In typical visual performance studies utilizing a single observer station, a test population or selected jury will be evaluated "serially". That is, an individual selected from the test population or jury will be positioned at the observer's position, and the test conducted for response. After that test is completed, a second observer will be selected, etc. The information, in total, would then be assimilated and assessed for general pattern and indications, etc.

The visual performance test installation is an experimental arrangement that allows systematic investigation of the lighting parameters that influence visual performance. The installation is designed to study the effect of the variables by carefully controlling the complete visual field-of-view so that one of the parameters can be changed without changing the other parameters. This means controlling the location and orientation of viewing or measuring position, the task position, light positions and the complete visual surround or background.

In order to conduct preferred visual performance tests the position and orientation of all of the elements should be controlled. One and only one of all the elements should have a fixed position and orientation while all of the other elements should be adjustable. One solution is to have the task position and orientation fixed. In this case, all other positions (viewing, measuring, lights and background) should be adjustable for two angular directions with respect to the task, one rotation angle about an axis from the location to the task, and distance or optical/electronic equivalent. While this is one possible solution for providing all of the degrees of freedom, it is not necessarily the best solution.

In some instances, a better solution is to fix the direction and rotational orientation of the viewing/measuring position, allowing only for changing the distance to the task. In this case, the task cannot be fixed and must be adjustable in two directional angles and rotation about one axial direction. The three axes of the sample holder should preferably be constructed so the transparent or translucent sample can be investigated for light transmission situations if desired. Complete degree of freedom can be maintained if one directional angle is removed for one of the remaining elements. For example, one of the light sources such as the primary task light. All other lights and background require distance, two directional angles, and rotational orientation if not circularly symmetrical about the axis to the task.

In some cases, to maintain a parameter constant, rotational motions must be linked. For example, when viewing a reflection in a glossy surface as the task is rotated, the reflected image moves. To maintain the image of the same reflection, the object that is reflected should move through twice the angle of the reflecting surface. Therefore, one of the features of the test fixture is a platform that moves at twice the angular rotation as the task fixture.

The primary viewer test is for task visibility. Lighting parameters are varied and the viewer makes a judgment on visibility of an object or characteristics. The conclusion of the process might be a responses such as yes/no, or threshold luminance, threshold angle, color limit, threshold glare or preference. Objective luminance measurements are made with a video photometer to determine the luminance distribution for both the task and the background. The light sources should have defined or measured characteristics with respect to luminance surface distribution, angular luminance distribution, spectral distribution and polarization. This is preferred since all source characteristics can influence task visibility. The viewer and lighting measurements are correlated to develop the specifications for optimum task lighting. Identification of Preferred Viewing Conditions In typical processes according to the present invention, it is preferred to define a threshold condition which can be used as a means of defining whether or not any given test is a success or failure, or at least is relatively better or worse when compared to some other condition. In typical processes according to the present invention, the threshold conditions will be defined in one of two manners:

1. Achievement of acceptable failure or error rates, in the identification by the viewer of items perceived as defective, etc.

2. If the process is one which concerns the completion of a task by a performer, the satisfactory performance of that task within some given time, preferably as short as possible.

The first type of threshold conditions will be most important when the process concerns, at least in part, development of conditions for the conduct of examinations, etc., for defective or undesirable items, such as manufactured items or materials. The threshold condition will be those conditions under which a desired or acceptable level of failure or error rates occur in the inspection. This will typically be identified by achieving a statistically desirable level of successful identification of defects, i.e. identification of items as defective which are in fact defective; and, a statistically desirable level of passage of items as acceptable, which are in fact acceptable. It is desirable, in general, both to have a relatively small number of defective items pass, and a relatively small number of items which are in fact not defective identified as defective.

The second type of threshold conditions will generally concern applications of processes according to the present invention in order to define preferred conditions for the performance of a task that does not concern the inspection of passing/failing items, but rather which generally concern the satisfactory performance of some task which needs to be completed. In general, in such situations a goal is to achieve operation of the task in as short a time as possible, and there is no particular concern with whether or not there is some item which passes/fails an inspection for cosmetic or structural defect. For these types of studies, the visual performance lab may include, instead of a sample holder, a work-bench or station at which a subject performs a task. The lighting directed onto the work station or in the environment can be varied to determine preferred conditions.

In general, after the visual performance lab is established, the next step is a visual performance study (i.e. a lighting/task performance investigation). The investigation is generally conducted by controlling the various lighting characteristics and measuring their effects on performance of the task. The performance measurements generally include disability, lighting and task performance. Task performance is a direct and objective performance measurement. Lighting is a direct physical measurement, while visibility is an indirect and psychophysical measurement of task performance for tasks requiring or benefitting visual imaging. When the tasks are visual defect inspections, visibility becomes the performance task. In such lighting/performance investigations it is preferred to control the visual characteristics of the visual environment. The lighting parameters include, but are not necessarily limited to, lighting angles, viewing angles, lighting source luminance distribution or pattern, lighting source contrast and lighting source color distribution. The experimental process would preferably include the luminous characteristics of the whole field of view, so that background adaptation, discomfort glare, disability glare and transient adaptation can be controlled and specified.

Visibility measurements are those which depend on the response of a human observer. The objective measurements are physical measurements that depend on the response of scientific instruments. The objective measurements which directly correlate with visibility are scene luminance distribution and color distribution. The type of instrument which best measure these characteristics is the video photometer. A video photometer system generally comprises a video camera, computer and special software for scene imaging capture and calculations. The video camera captures the scene image of interest. The computer converts the image file into luminance values (in some possible future equipment, color values). The software calculates various parameters of the visual object under analysis. One such system is the CapCalc system, referenced herein.

Visibility measurements are taken using juries, i.e. populations of individuals. In general, the jury should be selected taking into consideration the demographics of individuals performing the task, or identifying the threshold value.

In general, the next step in the process is to determine a set (or sets) of lighting specifications for all of the tasks based on the results of the lighting/performance investigations. This step does not necessarily specify the kind of lighting (for example, incandescent, fluorescent, metal halide) or the technologies to be used. There will in some instances be differences in the preferred lighting specifications for different task steps. The specifications are typically for lighting characteristics (for example, source luminance distribution, source spectral distribution, source directional distribution). That is, visual performance based attributes of the lighting system.

Interference

In general, once a number of preferred lighting configurations for various tasks that need be performed have been developed, it is desirable to determine the degree of interference between the lighting configurations, and the performance of the various tasks. The ability of the lighting configurations provide good visibility for defect depends not only on particular lighting, but also in the absence of other interfering lighting. For many defects, much ambient lighting is not only useless but is detrimental to the visual test because it can mask defects making them invisible. It is therefore desirable to determine the interference between the selected preferred lighting configurations. Where there is only sight or no interference, the lighting configurations could be used simultaneously. Where there is significant interference, the lighting configurations are preferably isolated either spatially or temporally. If the same individual is conducting the viewing under different lighting conditions, with significant changes in overall scene luminance, consideration must be made for the time required in transient adaptation, that is, for the viewer to adjust.

Design of the Viewing Station

A step of the preferred process is the designing of a task lighting system environment for actual implementation in the workplace, based on the lighting specifications found as the result of the laboratory investigations. Herein, this viewing station will sometimes be referred to as an "industrial viewing station" or "inspection station". While construction of this station can be complex if there are a number of different and conflicting sets of lighting characteristic specifications, in general the visual performance studies will identify the controlling one(s). In some instances, it may be necessary to develop conditions which are different for the performance of one part of a task or one step in a task, than are used in the performance of another. For example, one set of conditions may be utilized to examine the exterior surface of a car body for one type of defect (or one particular defect), whereas another different set of conditions might be utilized to examine or inspect the exterior body of a car for another type of defect (or different defect of the same general type). When such is the situation, generally one of two approaches will be implemented in the field:

1. Either the car will be moved from a first part of the viewing station to a second part of the viewing station during the inspection process, with the lighting conditions of the two parts of the viewing station being different; or 2. The car will be positioned at a viewing station which is an environment in which more than one lighting condition can be selected by the viewer, depending upon which phase of evaluation is being conducted.

In many instances, the development of field applications will involve or include allowance for different conditions to be established, depending upon the viewer. For example, it may be found that one set of lighting conditions enhances performance of one particular viewer, whereas a second set of lighting conditions is best for performance of a different viewer. When such is the case, lighting conditions at the viewing station may include controls for variance, to allow each viewer to select preferred conditions for that viewer's performance. This would be useful, for example, when different viewers are utilized in different shifts, to view at the same viewing site of an industrial facility. Microprocessor controls of the lighting and background conditions may be used to facilitate the operation of this task. For example, through use of appropriate computer programs each viewer's preferences can be stored in microprocessor control equipment, so that they can be readily established through a microprocessor control, simply upon entry by the viewer of an appropriate code or designation. Conventional computer equipment and control programs and devices can be used for this.

In addition, controls allowing variance in lighting and background at any given station may be utilized so that a given viewer can change the conditions, if viewing of more than one defect is desired and it is found that viewing for the different defects is facilitated by different lighting conditions. Thus, a viewer positioned at a viewing station may set the lighting and background controls to a first setting or condition for conduct of a first viewing of an object, and at a second setting or condition for conduct of a second viewing process. Again, conventional microprocessor controls and equipment can be utilized to facilitate performance of this. In addition, conventional timing and microprocessor controls can be utilized to cause automatic adjustment between or among the various settings.

In addition, in some instances it may be found that different lighting characteristics are preferred just based upon the color of the object. In assembly lines wherein objects of various colors are passing through the viewing station with time, it may be desirable to have control systems which allow lighting conditions to be varied either by the inspector or automatically, depending upon the particular color of the object to be viewed. Again using the example of a new car exterior evaluation, one set of lighting conditions might be utilized for white cars, whereas another set of lighting conditions might be utilized for a dark colored vehicle, in performance of the same viewing. Appropriate controls, implemented with conventional components, at the viewing station can be utilized to allow for either manual selection or automatic selection between or among the various lighting and background conditions, to facilitate the viewing process.

Selecting the lighting type and configuration for the viewing station is based in part upon determination of optimum lighting conditions for performance of the task, obtained in the studies using the visual performance lab.

The preferred (sometimes optimum) lighting configurations obtained in the visual performance lab may be only a relative optimum, since the cost determining absolute optimum may be prohibitively expensive or not possible due to the available equipment.

It is not necessary that the viewing station be designed to implement precisely every optimum (or preference) determined in the visual performance lab. In general, the process can be used to make significant improvement in test performance through better lighting.

It is noted that in some instances industrial viewing stations will be constructed around moving objects, and others for use around stationary objects. Sometimes, detection is facilitated by movement of light over the object being evaluated. When the object itself is moving, in many instances this is accomplished with stationary lighting. However, when the object is stationary, such effects can be accomplished either through sequencing of lights or light banks, or movement of lights. It is foreseen that instances in which relative movement of the object to the light, with respect to the viewer, is most useful, will be those in which a lighting pattern shown on the object is used, and its movement helps define irregularity or discontinuity (i.e. defect).

Viewing Stations—Generally

In general, the term "viewing station" or variants thereof used herein is meant to refer to a lighting station positioned in the field, for example at an industrial site, for conduct of the visual task. In general, task viewing stations according to the present invention will include appropriate equipment positioned for implementation of the preferred parameter determined as a result of a visual performance study. A typical viewing station will include some form of framework or rig, in which various lights and lighting equipment can be mounted. It will in general include at least one observer station, and appropriate control equipment for the lights.

In many instances, preferred task viewing stations according to the present invention will be characterized as including appropriate lighting equipment and lighting equipment controls, so that more than one set of lighting conditions can be created. This might include, for example, microprocessor or automatic control system, to switch between a first set of lighting conditions and a second set of lighting conditions. These would facilitate performance of more than one form of detection, or detection of more than one form of defect, at the same viewing station. Conventional framework materials, light sources, control equipment, etc. can be used as components in viewing stations according to the present invention.

It is foreseen that many task viewing stations according to the present invention will include equipment providing for more than one lighting or lighting system type. For example, point sources of light and line or box sources of light may both be provided, with controls allowing for ultimate selection between them. Different color choices, levels of polarization, etc. may also be provided. In addition, different directions or intensities may be provided.

Many task viewing stations implementing preferred values from visual performance studies according to the present invention will include glare and veiling reflection reduction materials or equipment. These may include, for example, surround curtain panels, etc. in order to block exterior environment glare. They may also include baffles and lenses on lighting systems, custom lighting fixtures, highly controllable fixtures and limits on surround luminance. Control of general area light sources may also be used.

It is foreseen that in many instances, programmable equipment for selective control of the lighting conditions will be preferred. This can be accomplished utilizing conventional microprocessors or computer equipment.

In some instances, the visual surround system should be static, in others it can be changed depending on the particular viewing task being performed. Often the visual surround system will include means for blocking outside light; and, a luminous surface directed toward the object to be viewed.

In many instances, pattern systems either for direct reflection or for projection onto the object being investigated, or for the visual surround area, will be desired. This can be accomplished utilizing a variety of conventional equipment, for example video monitors, filters, etc. Also, patterned surfaces, made luminous by direction of light thereon, can be used. In many instances it will be desirable to have equipment that allows for change in the visual surround pattern, on a selected basis.

In many instances, it will be desirable to having lighting equipment positioned such that it is selectively adjustable, as desired. Conventional equipment such as various servomechanisms or mechanical arms, jacks, etc. can be used to accomplish this. Again, microprocessor controls, using conventional computer equipment, can be installed.

In general, among the many possible approaches to the task viewing station design that are possible, studies according to the present invention can be used to specifically implement them based upon a variety of concerns such as, for example: a visibility-based system, based upon the visual abilities or acuities of the persons involved in performing the task; systems based on minimizing or at least controlling visual stress and fatigue throughout the work period; systems designed to facilitate viewing of contradictory tasks, i.e. more than one task each of which is best visualized under different circumstances; etc. It is also foreseen that with the implementation of automatic sensing equipment, etc., lighting systems can be designed which are self-adjusting, based upon either preselected logic program or some sensed parameter.

In some instances, the arrangement can be designed to facilitate energy savings, by providing for minimal necessary light for adequate performance of the task.

As explained above, various systems can be designed for either providing fixed images on moving objects, or moving images on fixed objects, depending on the needs. For example, to simulate light movement, a bank of lights in sequence can be utilized. Of course, a mechanical arrangement that allows for actual movement of lights could also be used.

Many systems according to the present invention will be specifically designed for performance based on a limited demographic. That is, the systems will be designed specifically to facilitate the viewing by a selected population, rather than the general population at large. This will enhance performance and in many instances energy savings.

An Example of a Viewing Station

Figure 3:
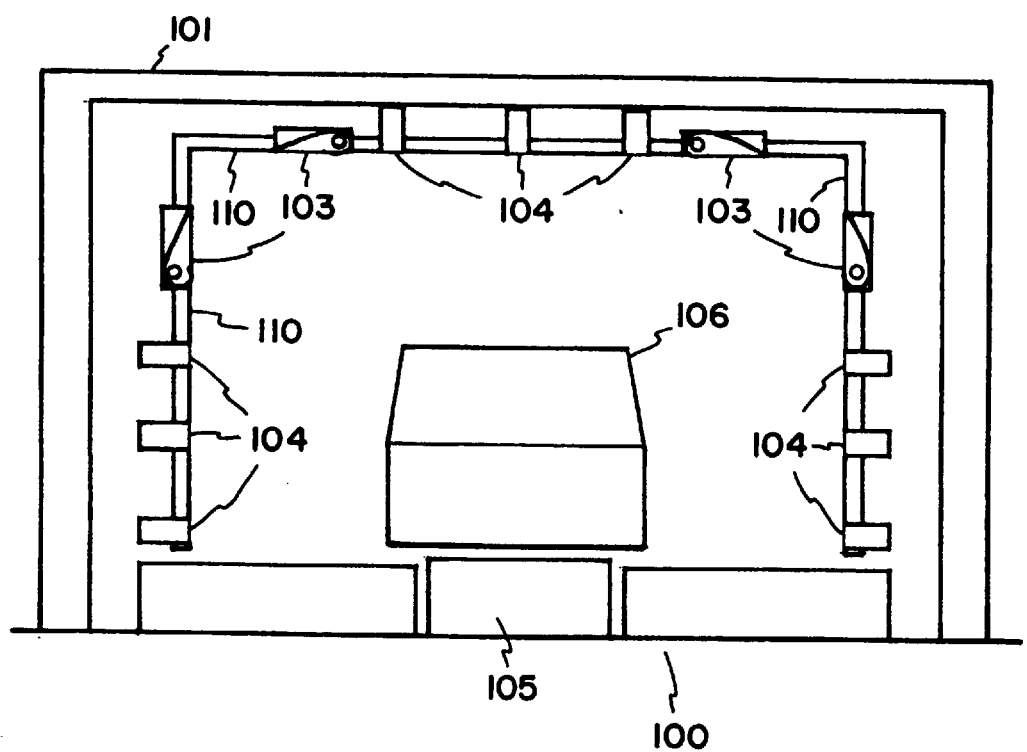
FIG. 3 is a schematic end elevational view of an industrial viewing station according to one embodiment of the present invention.

Reference numeral 100, FIG. 3, represents a viewing station usable for example with vehicles in an automotive assembly. The station 100 includes a tunnel shaped rack 101 having various lighting systems 103 and 104 therein. Arrangement 100 includes track 105 on which vehicle 106 is positioned for movement. The rack 101 defines a visual surround and has an interior in which an object to be viewed is positioned.

Lighting system 104 comprises a plurality of incandescent, i.e. point source, lights oriented to direct lighting against various points of the vehicle 106, i.e. the top and sides. Lighting system 103, on the other hand, comprises quartz asymmetric lighting systems for use in surface illumination of the visual surround.

On surfaces 110 of the visual surround or tunnel are positioned luminous visual patterns, typically bidirectional grids and other linear or non-linear images or patterns.

In use, the asymmetric systems 103 are used to light the surfaces 110 of the tunnel. This will cause the pattern of the tunnel walls to become a luminous light source which can be reflected on the vehicle 106. This can be used, for example, to detect contour-type (i.e. dimensional defects) of the vehicle 106.

On the other hand, directional lighting sources 104 are intended to directly illuminate the vehicle 106 to enhance detection of defects.

In some operations, systems 103 and 104 might be used simultaneously. In others, they may be used at different points in time, to facilitate defect detection. of course, in some lines, there might be only positioned horizontally directed lights or vertically directed lights, depending on what portion or portions of the vehicle 106 is being evaluated for defects. In addition, the various lighting equipment can be positioned spatially separated, to facilitate detection.3

An Example of a General Implementation

Consider a situation in which all of the defects of interest can be sorted into two groups, for which as a result of a visual performance lab study it has been determined that there are two preferred lighting configurations, for conduct of the detection; that is, a first lighting configuration for the first type of defect, and a second lighting configuration for the second type of defect. Further assume that one of the lighting configurations is a patterned luminous source and that the other lighting configuration provides a single direction illumination with restricted illumination angles. Further assume that the object to be viewed is small and can be manually manipulated.

For such assistant, the lighting arrangement at the viewing station may include a pattern panel with relatively uniform luminance and a single spotlight to provide single direction illuminance. Since these two kinds of lighting configurations usually strongly interfere with one another, they could be separately located (and the object moved between them) or they could be independently controlled, with a mechanism for switching between them. If the item is relatively large, the lighting system could include a uniformly luminous visual surround, with the appropriate pattern and an array of spotlights located so that each part of the item is illuminated predominantly by only one of the spotlights. If the large items are on a moving line, the surround can take the shape of a tunnel. Typically, control will need to be provided in this later instance due to the strong visibility of interference between these two types of lighting configurations. For example, one may totally mask the other.

Assuming that what has been determined as a result of the study in the visual performance lab is that one of the lighting configurations that should be implemented in the viewing station is a pattern luminous source, at issue is how the pattern luminous source should be implemented. A simple approach is a pattern on a surface properly located with respect to the item under visual inspection. If the pattern is on a opaque surface, it can be illuminated from the front side. When front illumination is used for pattern illumination, it is important to locate the illuminating sources so that disability glare is minimized. This requires the illuminating source not to be in the field of view of the observer. It is also important that direct specular reflection of sources in the item under inspection also be carefully controlled On the other hand, if the pattern is on a translucent surface it can be back illuminated. Fixed pattern technology allows only limited control of the luminous pattern. The luminance of the pattern can be changed by controlling the level of illumination on the panel surface. In this manner, color can also be controlled by changing the color of the illuminating source. Control can also be provided to illuminate only those parts of the panel that are appropriate for observing that part of the item that is presently be observed for defects. This can be important if parts of the luminous pattern that are used for visual detection of other locations of the item under inspection interfere with part of the pattern that is being used for visual inspection of the defect under observation.

To reduce the interference due to different parts, one can utilize technology that will direct illuminance only to the desired locations of the item under visual inspection. For example, baffles, columnators, lenses and holographic defusers can be used. More specifically, the light can be controlled to as tight an angular distribution as desired, either circularly or in planes of distribution.

Projection systems can be used to accommodate defects that require different pattern geometries or changes of more than a single color. The projection patterns can be either on the front side of an opaque panel or the rear side of a translucent panel.

Above it was indicated that the other lighting configuration in the example would be a single direction lighting. Again there are multiple technologies that can be used, depending on the requirements for direction and divergence. Single directions can be approximated with spotlights, if they are not too close to the item under inspection. Lasers can provide very low beamed divergence. Lenses can be used to improve the beam characteristics of small light sources. If defects require different illuminating directions, multiple light sources can be used with controls switching between the different illuminating directions. Color control can also be incorporated using a variety of techniques such as filters.

If the item under inspection has high reflectivity, the reflected light can be reflected again from the surround and therefore become a source of interference lighting. For an array of small light sources providing single direction illumination, this interference can be reduced by a surround of low reflectivity. This would also effect background luminance.

The concepts discussed above can be extended to any number of general lighting configurations. This could include, for example, consistent configurations as an unpatterned surround of uniform luminance and light sources with beams in a single plane.

C. Jury Selection

Measurement of visibility using a jury (or test viewer population) should involve selection of a jury taking into consideration the demographics of the appropriate inspection population. As indicated above, in some industries visual evaluation is a senior position and the viewers are older persons, with decreasing visual capability. If such is the case, in some instances such persons, or at least persons of similar age, should be utilized as members of the jury or test viewer population.

If the jury is being selected in order to evaluate consumer identification of thresholds at which defects are perceived, it is preferred to utilize as the test viewer population a jury of individuals belonging to the population of the anticipated purchasers/end users. If a product is one which would typically be purchased by persons over 50, a jury reflecting that demographic is preferred for the Lest viewer population study. With respect to this latter, it is noted that interesting threshold patterns will be observed in some industries. For example, if the product involved is a large luxury automobile, most likely to be purchased by an older population, even though there may be a theoretically lower threshold tolerance for cosmetic defects, due to the high investment involved, the end user/purchaser population may possess less visual capability than the population generally, and thus be less likely to identify a variation or perturbation as a defect.

Some General Observations from Lighting Tests Conducted with Juries

In general, studies conducting principles disclosed herein have led to the development of certain general principles concerning defect detection. For example, when an object is properly illuminated, it has been found that defects are generally visible at very low illumination levels, in preference to higher illumination levels. By "very low" in this context, it is meant under 200 LUX. This is a level of 10% of the intensity of many present industrial inspection areas. In general it is believed that this results because glare has been reduced and task contrast has been enhanced. It appears to be most pronounced when area lighting is controlled for glare and special viewing lighting is oriented properly and shielded for glare.

Also, when an object is not properly illuminated, defects can be invisible even at very high luminous values; for example, due to failure to optimize on a dimensional defect.

Thirdly, different kinds of defects require different lighting configurations for good visibility. An example of this was discussed above, in connection with comparing evaluation for dimensional defects versus non-dimensional defects, and also in connection with discussions concerning the properties of the surfaces being illuminated. In addition, different colors and finishes often require different lighting settings.

Fourthly, a defect may have good visibility for more than one kind of lighting configuration. For example, contour dimensional defects can be seen both from grazing light casting a shadow and by distortion of a reflected image.

It has been found that the illumination level for good visibility is generally non-critical, provided the lighting is otherwise appropriate for the task, and comfortable. That is, once threshold illuminance is passed and reasonable adaptation luminance is maintained, good visibility is maintained until the light level approaches a level of discomfort or excessive glare. However, higher levels do result in viewer fatigue and energy inefficiencies.

Finally, it has been found that disability glare clearly is a serious problem for many defect/lighting configurations. That is, bright light sources in the field-of-view decrease the ability to see the task and create an uncomfortable viewing situation.

IV. Some Industries of Interest

In general, as a result of analyses in part using techniques discloses herein, some general principles applicable in various industries have been developed. In this section, some industries in which processes according to the present invention will be useful are briefly evaluated. From the general presentations, applications in other industries will be apparent.

A. Polymeric Components—Tire Industry, Brake Liner Industry, etc.

In the automotive tire industry, especially new tire industry, it is necessary to evaluate the insides of tires for structural defects. In general, defects in the internal core are sometimes viewable by defects in the surface material. In addition, surface structural defects such as cuts and tears may need to be evaluated.

Such an evaluation does not generally concern consumer threshold studies. The defects are generally not merely cosmetic, and principally concern quality control at the manufacturing plant in order to obtain a product (for example, a tire) not subject to an unacceptable failure rate or risk of failure. A similar situation exists with polymeric material such as radiator hoses, brake linings, belts, etc.

Such materials are generally not very glossy, and are often very dark colored or black. The flaw or defect for which examination is being made are generally the same color as the remainder of the material, and comprise variations or flaws in the material (indicating mechanical damage). In general, these dark tasks of low specularity require high levels of illumination and very severe glare control.

B. Cast Metal Objects

A great many industries rely upon parts that are made through casting processes, for example engines in many vehicles comprise aluminum castings. Often it is necessary for the castings to be inspected for hot tears, or similar structural defects, after the casting operation. Metal cast items often have properties of substantial glossiness and are often complex shapes. Defects being evaluated are typically of dimensional type. Thus, in general contrast enhancement by light position control is useful.

C. Cosmetic Defects—Glossy Finished Surface

An example of this type of defect was discussed above, in connection with surface defects appearing in glossy exterior finished surfaces of vehicles. Both non-dimensional and dimensional defects are of concern. Because the defects are generally cosmetic, in many instances an initial study will be preferred with an end user/purchaser based jury, in order to develop threshold values.

In general, since highly glossy surfaces are involved, typically glare becomes a significant issue and pattern technology is often useful (for example, border interference). Since the products may be manufactured in a variety of colors, typically light levels and lighting positions may need to be adjustable. It is foreseen that lighting stations will eventually automate lighting placement and levels via sensors and computers.

Other industries subject to similar concerns include those involved in the manufacture of boats, buses, trailers, mobile homes, snowmobiles, motorcycles, etc. It is noted, however, that the threshold level acceptable by the purchaser/end user may vary, depending on the item involved. For example, the threshold for appropriate defect identification is extremely low in the motorcycle industry, whereas it may be relatively high when the surface involved is the roof of a bus. This is because in general motorcyclists are observed to be extremely particular about the appearance of the painted or finished surfaces on their vehicles, whereas the roof of a bus is generally not even in view when the purchase is made and, in many instances, the purchaser does not inspect any given bus for cosmetic defects to anywhere near the same extent as a motorcycle purchaser, especially when the bus purchaser is a city or governmental agency purchasing a fleet of buses for operation.

D. Finished Surfaces—Non-glossy

In many instances, finished surfaces are involved which are generally not shiny or glossy. Products such as appliances often have such surfaces. In some instances they are stippled in some manner or have a matte finish, and thus do not reflect light as clearly as the metallic, gloss finish of an automobile. In many instances, white or light colors are involved with such products.

In general, defects on the products are dimensional and are found by careful angular control and glare limitation.

E. Transparent Objects

In some instances, the object to be inspected is transparent or substantially transparent. For example, window glass or structural glass needs to be inspected for both cosmetic and structural defects, sometimes by the manufacturer of the glass, sometimes by an installer, and sometimes by the end user. In general, especially if window glass is involved, it is important to understand that the end user, i.e. the occupant of the building in which the glass is placed, will in some instances be viewing very bright light (sunlight on a bright day) through the window, and in other instances will be viewing relatively low light conditions, i.e. dusk, etc. Extremely bright conditions such as a very bright sky, etc., differ substantially from the conditions in almost any factory. In addition, the end user views varying scenes through the window that may differ greatly in color, contrast, and amount of light by comparison to a typical industrial environment.

In general, visualization of defects in glass and other transparent objects can be optimized at least in part by providing a viewing of colored, and preferably contrasting or patterned images, through the item. What the viewer sees, then, is a distortion in the viewed surface or image, rather than a distortion in the transparent surface itself. It is found that in general, scenes such as geometric grids with dark and colored backgrounds will typically be most useful, as the background scene in a viewing process of this type, as opposed to a complex geometric pattern. A reason for this is that contrast is enhanced, i.e., image distortion is more easily distinguished from the background.

F. Structural Shape and Conformity with Specifications

In some industries it is necessary to establish that a manufactured item is appropriately flat or appropriately curved, or in some other manner conforming with specifications. Shape or configuration, for example, can be very important with respect to such products as circuit boards, computer disk drive components, and other manufactured items. Variations from appropriate conformation are generally dimensional defects, and can be visualized utilizing the techniques described herein as generally preferred for dimensional defect detection.

G. Finishing Techniques and Materials

In some industries, paint finishes, lacquers, etc. are utilized in part to mask cosmetic defects in the underlying surface. Techniques according to the present invention can be utilized to evaluate success in achieving this, by development of appropriate test samples for comparison utilizing the evaluation techniques described. For example, objects possessing cosmetic defects may be painted with a variety of colors, or using a variety of paint techniques, and then tests can be conducted to determine which material or technique is most successful and best avoids the end user/purchaser continuing to detect the defect or identifying the item as defective.

V. Investigation Procedures and Protocols

The following procedures and protocols may be utilized, for collection and utilization of information while applying techniques and methods according to the present invention. Of course, variations in the procedures and protocols may be utilized, as applicable to specific instances.

The Visual Task
1. Select a specific job description.
2. Select a series of employees performing this job who represent a range of employees (and the oldest age range) performing the job.
3. Interview employee and observe task performance to develop a description of the visual task.
4. Describe, in detail, all of the visual elements of the task.
5. Describe, in detail, the range of difficulty of each of these tasks by having the employees rate them numerically.
6. Formalize a visual task description including the priority of difficult task elements.
7. Select or manufacture samples (objects to be viewed).
8. Measure visual task elements with an instrument such as a Sheffield Proflicorder for both planar length and width and 3-dimensional size.
9. If visual task is observable by a consumer as a potential product defect, determine consumer thresholds for cosmetic complaints.
10. If task performance exhibits failures of certain types, determine visual threshold for failures for the demographic viewer group in question.
11. Summarize findings.

The Visual Environment
1. Define the current task viewing environment in terms of lighting use and placement and contrasts in the visual surround.
2. Define any other relevant viewing environment, such as difficult viewing positions, other environment conditions such as noise.
3. Select a series of employees performing this job who represent range of employees (and the oldest age range) performing the job.
4. Photometrically map each of the viewing environments with a device such as the IQ Cam video photometer available from the National Research Council of Canada. Another useable device is the CapCalc system also developed by the National Research Council of Canada.
5. Measure luminance ranges of the task and the local area and the visual surround.
6. Measure and calculate discomfort glare and veiling glare levels.
7. Assess transient adaptation in these environments.
8. Determine which parts of the current visual environment are detrimental to task performance due to adaptation, glare and large luminance ranges. This information will be carried forward.

The Visual Process Assessment
1. Select viewing subjects of the relevant demographic mix.
2. Test visual acuity.
3. Fix a sample of a visual task selected above on the visual task positioner. Alternatively, place sample where it is most accessible for viewing studies.
4. Fix the primary task light at an appropriate angle to illuminate the sample. If lighting is indirect, the source of illumination is the surface of reflection.
5. Turn the primary task light to a comfortable level, for example, 100–1000 Lux.
6. Instruct the subject to orient the task sample to optimize task viewing with only the illumination lighting on. Alternatively, orient the subject so that task viewing is optimized.
7. Alternatively, test subject at many angles and determine optimum angle.
8. Next, instruct the viewer to turn the illumination down until he/she can no longer see the visual task.
9. Alternatively, test subject at threshold for a range of angle and determine optimum angle.
10. Next, instruct the viewer leave the illumination on at minimum viewing and level to turn up masking illumination or other relevant masking illumination until he/she can no longer see the visual task.
11. Alternatively, block or filter masking illumination moving from less masking to more masking until subject can no longer see the visual task, if possible.

The Visual Surround System Development
1. Select viewing subjects of the relevant demographic mix.
2. Test visual acuity.
3. Select subjects (representatives of the demographic group).
4. Develop a series of patterns and grids for experimentation of linear and non-linear distortion testing.
5. Fix a sample of a visual task selected on the visual reflection holder or on the visual task positioner.
6. Place the holder or positioner adjacent to the pattern selected and visually scan the visual task for relevant detail.
7. Repeat the process for ranked comparison of ease of task detection via the use of linear and non-linear grids, patterns, and other images.
8. Determine which patterns, if any, provide a task viewing benefit for the viewer.
9. Summarize findings.

The Lightinq System and Development
1. Select a job description for this project
2. List all visual tasks which are being performed by the employee at this position.
3. Assemble all of the viewing parameters which were gathered under the visual process assessment for this task.
4. Determine which task viewing parameters for various visual tasks are similar to one another, and create clusters of similarly viewed tasks.
5. Select a viewing position and visual task position in the experimental lighting grid system.
6. Set up lighting in the lighting grid to comply with viewing experiments under the visual process assessment for each of the clusters of optimized viewing parameters.
7. Program the lighting system to separately control each similar viewing cluster lighting and set each system level significantly above the visual thresholds established.
8. Insure that all lighting does not violate the visual stressors defined in the visual process assessment.
9. Select and install the visual surround using the optimized finishes and lighting determined in the visual surround system development phase. This is only done if the visual surround phase has shown specific benefits in task viewing.
10. Select and install the visual surround using the optimized patterns determined in the visual pattern surround system development phase. This is only (done if the pattern visual surround phase has shown specific benefits in task viewing.

11. Experiment with the lighting system, using each of the task samples used earlier in the experiment, and adjust the system to optimize visual performance using photometric measurement and subjective, demographically correct viewing experiments.

12. Summarize findings.

The System Adjustment and Programming

1. Install lighting system and surround, if required, in the appropriate task setting.
2. Inspect installed system for correct execution of the design intent.
3. Program the system based on the parameters selected in the Visual Performance Laboratory experiments.
4. Program the order of lighting settings (scenes) and their manual or automated control in sequence and in time.
5. Program the control system to receive information from the visual task, if available, such as color, reflectance, etc. which may be in the task data base which is referenced to the code numbers or part numbers on the task (ex. automobile computer ID tags).
6. Check the system with all visual tasks used in the laboratory research, and adjust as needed.
7. Train visual inspectors on the operation of the system and continue to monitor and adjust the system to deal with issues not determined in the laboratory research.

Mathematical Models of Visual Task Visibility

Based on information developed in the database regarding the relationship between task attributes and viewing performance, a mathematical model of task visibility can be developed for any visual task.

Computer Simulations in Lieu of a Physical Visual Performance Lab

There are now available computer programs that can very accurately represent visual images of objects and finishes. An example of one of these computer programs is Lightscope, available from San Jose, Calif. With one of these computer programs, an operator can selectively modify or control photorealistic images of an object in three dimensions. Thus, color, light, contrast, finish and shape can be represented and modified as selected by the 20 operator. With this means, products can be constructed, such as automobile bodies.

Of course, in using these programs, a programmer can program into the image a defect, mimicking measured defects or evaluated defects in actual products. Thus, with a program, the operator can simulate lighting conditions to determine how well the programmed-in defect can be visualized.

Such techniques are generally referred to herein as visual lab simulation techniques. By using a database depicting objects with various finishes and defects, especially under various lighting conditions, the software can be used to simulate the physical visual performance lab. Thus, a jury can be positioned at the computer console and shown various images for determination of preference. Additionally, the visual characteristics of the viewer can be programmed into the system as well as the demographics of an anticipated population and their viewing characteristics. Thus, within such programming one can develop a conceptual and mathematical model that will predict the visibility of the visual task independent of the observer and rate that task for its capability for any given demographic. With this, one can generate proposed, preferred, viewing stations for implementation at industries.

EXAMPLE—

Automobile Inspection

The intent of this experiment was to define visual defects, determine how they are viewed, and to optimize the lighting and the visual surround related to this task. The strategic goal was to improve defect detection and to lower inspection problems. This work involved the assessment of a series of defects, the design and construction of an in-lab automotive inspection line lighting prototype and an initial look at existing and some new lighting types.

An in-depth set of findings and views regarding the inspection process was developed. Underlying these views was a survey of inspectors' views, measurements within the facility and lab studies.

The inspector surveys included questions on visual problems and fatigue, lighting quality and inspection procedures, training process and vision correction. These surveys demonstrated clearly that a significant percentage of inspectors are visually fatigued or have visual problems. Copies of the survey and a chart of results are included as Tables 2 and 3.

In-plant measurements were completed with a CapCalc video photometer system (available from the National Research Council of Canada, Ottawa, Canada) and were used to obtain luminance values in the field of view of the viewer. Typical luminance values from these types of measurements are shown in Table 1. These demonstrated high levels of brightness in the field of view with large dynamic luminance ranges beyond those in reasonably controlled viewing environments. They also confirmed very high illuminance values from the lighting systems.

Lab studies were intended to assess the viewers visual performance when observing visual defects typical of those exhibited on auto bodies. Viewers were assessed in terms of optimal viewing angles, threshold luminance detection ranges, sensitivity of visibility to direct glare and sensitivity of visibility to masking illumination.

Following the subjective experiments, objective measurements were taken to document each of the successful subjective viewing conditions in terms of surface luminance and illuminance. Gloss measurements were also taken in order to find out the range of gloss of the various surfaces, including samples of painted finishes.

laboratory measurements

Laboratory measurements on lighting defects were performed with the aid of a test fixture generally according to FIG. 1. The fixture held the samples and could orient the direction of the sample by rotation about three different axes. All observations and measurements were made from a single fixed direction. The test fixture has an arm for mounting light sources. This arm can rotate through an angle of almost 180 degrees. Measurements were made on a numerous samples with a range of colors, finishes and defects.

Test Procedures

For visual observations, a sample was selected and mounted in the test fixture. The horizontal axis was set at 0 degrees. A single task incandescent lamp was mounted in a holder on the lighting arm. The lighting arm was set at a fixed angle with respect to the reference or observation direction. All of the observations were made under these limited conditions so that these measurements are only indicative of the total range of lighting conditions that should be investigated.

The observations were made from a viewing station that had a fixed viewing slot so that the observer was restricted to viewing the sample from a controlled direction. The observer would then rotate the sample about the vertical axis, noting at which angles the defect was visible. Many of the defects could be seen over only certain angular ranges. The sample would then be turned to the center of the angular ranges for which the selected defect was visible. The observer would then decrease the luminance of the task light with a dimmer circuit until the defect was no longer visible. This determined the task light threshold illuminance for this particular defect, source light, source direction, viewing direction, viewing direction and viewer combination.

The next measurements were to determine the effects of additional lights on the sample defect and glare light in the observers field of view. Two additional incandescent lamps were mounted on the viewing station at approximately a fixed angle horizontally on both sides of the viewing direction. Since addition lighting frequently made the defect less visible, these lights were called masking lights. Another incandescent lamp was mounted inline and above the sample aimed in the direction of the viewing slot. This light is referred to as the glare source.

To measure the effects of masking and glare lights, the task light luminance was first set above the previously determined threshold. With the glare light off, the masking lights were increased in luminance until the defect was no longer visible. The illuminance at which the defect became invisible was called the masking threshold. Then with the masking lights off, the glare light was increased in luminance until the defect was no longer visible. The illuminance at which the defect became invisible was called the glare threshold. It must be remembered that these thresholds are only for a particular defect, source light, source direction, viewing direction combination.

The luminance of the task, masking and glare lights were controlled with dimming circuits. The levels were recorded by means of a digital voltmeter on each of the circuits. Measurements of the illuminance at the surface of the sample were made at several voltages for each of the different lamps used for task and masking lights. The illuminance from the glare light source was measured at the viewing slot of the viewing station. Illuminance curves were derived from these measurements and used to determine the illuminance in the threshold experiments.

Sample luminance was measured with the CapCalc video photometer system. The CapCalc images were taken for the viewing conditions used for each sample in the masking and glare threshold experiments. The CapCalc system was also used to measure the luminance of the glare lamp source. An example of typical data taken by these test measurements is shown in Table 5.

Gloss of the samples was measured with a Gardner Glossgard II gloss meter. This instrument measures gloss at an angle of 60 degrees. Typical gloss data is shown in Table 4.

There was a very large luminance range and probably creates transient adaptation problems. As expected these luminances are higher than the scattered light luminances and do not vary as much between the different colors as the scattered light. Other luminance examples are shown in the second part of the table 2 for the fluorescent lights, walls, floor and distant factory background.

General Conclusions from the Study

The defect measurements in these tests were limited to a single light source-viewing angle combination. In addition, for the most part the tests were conducted with only one task light source. Also, the defects supplied were only examples of defects. They were not calibrated and probably did not comprehensively represent the complete range of possible defects or of threshold defects. Therefore, these initial results were considered exploratory rather than comprehensive. However, even with these limited measurements a rather clear picture of the inspection light problem was developed. One of the most important results was that the quality of lighting was found to be dramatically more important that the level of lighting. If a defect is properly illuminated, it is visible at strikingly low levels of illumination. And if the defect is improperly illuminated, no level of illumination can make it visible.

A second important result was that different defects require different kinds of lighting. The lighting that might make one kind of defect very visible, could very well make another kind of defect invisible. While defects can be seen at low lighting levels and high lighting levels create a multitude of visual task problems, no attempts were made in this program to determine optimum lighting levels.

One of the important results of the study was the beginning of a systematic understanding of defect types and characteristics. Defects can be characterized as having 35 one or both of two defect characteristics. The first defect characteristic is a change in the contour of the surface from the expected or normal contour. The second defect characteristic is a change in the reflection properties of the surface from adjacent or normal reflection properties. All defects investigated have one or both of these characteristics.

This classification of defects is important to developing an understanding to optimum illumination of auto finish defects. A preliminary understanding is that these two different defect characteristics require very different kind of lighting for good defect detection. Defects that have a contour characteristic can be detected and observed by the distortion of an image reflected from the painted surface. Indeed, for contour-only defects on black surfaces that is the only means presently known for effective detecting of defects. If the image distortion is severe, the defect is detected as a scattering center and is referred to as image scattering. Contour defects can also be detected by using grazing incidence light to produce a shadow.

For non-contour defects, it is very difficult or impossible to see the defect by reflected defects the best lighting appears to be single direction lighting. That is, the defect is illuminated by a single small light source and all other lighting is eliminated or suppressed,. This conclusion is preliminary and probably will not hold for all reflectivity defect types.

Initial Light Settings

An important aspect of the study was based on the conclusion that two types of defects (contour and reflectivity) require different kinds of lighting. For contour defects the study supports using direct fluorescent lighting at reduced luminance for all colors and finishes. This should be supplemented by a small amount of indirect lighting. There are presently no results that would indicate that the level of this direct lighting should vary with finish color since all colors have very similar gloss or specular reflectances. It is expected that in the future, for non-contour defects, that indirect fluorescent lighting illuminating specified image patterns on the visual surround will be appropriate. Future research could lead to even more systems and recommendations for contour type defects.

For non-contour defects the study supports using direct incandescent lighting. In this case the study supports a recommendation that the illuminance level vary with finish color since the defect luminance is dependent on the scattered light which varies significantly from white to black. Although these types of defects appear to be best illuminated with single direction lighting, there are probably exceptions which may require a modified, combination or different lighting system.

TABLE 1

Typical product background luminances example

| PRODUCT | | REFLECTIONS OF LIGHT | |
|---|---|---|---|
| COLOR | RANGE [cd/m$^2$] | AVERAGE RANGE [cd/m$^2$] | PEAK RANGE [cd/m$^2$] |
| 1 | 200–900 | 200–6000 | 1800 |
| 2 | 50–400 | 300 | 850 |
| 3 | 20–60 | 200 | 500 |
| 4 | 10–100 | 300 | 800 |
| 5 | 2–55 | 350 | 700 |
| 6 | 10–50 | 350 | 600 |
| | | RANGE | PEAK |
| LIGHTS | | 1000–8000 | 9000 |
| WALL | | 100–1200 | |
| FLOOR | | 100–2500 | |
| DISTANCE | | 20–250 | |

TABLE 2

Survey of inspectors - example

| | Min. | Max. | Ave. |
|---|---|---|---|
| Age (years) | 44 | 56 | 50 |
| Inspection Experience (years) | .5 | 10 | 5 |
| Have visual problems | | 23% | |
| Suffer visual fatigue | | 20% | |
| Have headaches | | 5% | |
| Wear eye glasses | | 30% | |
| Wear contact lenses | | 20% | |
| Formal inspection training | | 20% | |
| High quality of lighting | | 30% | |

TABLE 2-continued

Survey of inspectors - example

| | Min. | Max. | Ave. |
|---|---|---|---|
| Difficult inspection procedure | | 35% | |
| Number surveyed | | 20 | |

TABLE 3

Questionnaire for Inspectors:
Date:_____ Number_____ Station: Inspection
Results of this survey are kept confidential and will not be used for any evaluation of individual employees. In this research, employees will be referred to by number only.
Name:
Age:
Years of Inspection:
Visual Problems:        Yes_____    No_____
Fatigue:                Yes_____    No_____
Headaches:              Yes_____    No_____
Glasses:                Yes_____    No_____
Contact Lenses:         Yes_____    No_____
Formal Training:        Yes_____    No_____
Quality of Lighting:    High_____   Medium_____
Low_____
Inspection Procedures:  Difficult_____   Medium_____
Easy_____
How often are you uncertain as to whether something is a defect:
    0–5%_____   5–30%_____   30% & over_____
What is wrong with the current inspection process?:
What is wrong with the lighting?:
What changes do you think should be implemented?:

TABLE 4

DETECTION ABLE, DETECTION METHOD AND GLOSS DATA

| | | Gloss | Detection Angle | |
|---|---|---|---|---|
| Color | Defect | [%] | Min. | Max. |
| 1 | Type 1 | 70 | 50 | 60 |
| 2 | 2 | 60 | 45 | 50 |
| 3 | 3 | 50 | 1 | 70 |

TABLE 5

Example of Typical Data

Threshold Illuminance [fc]

| | | | Task Lighting | | | At Angle | Masking Lighting | | Glare Lighting | | At Task Illumi- |
|---|---|---|---|---|---|---|---|---|---|---|---|
| Sample | Color | Defect | Aver. | Dev. | * | [°] | Aver. | Dev. | Aver. | Dev. | nance |
| 1 | 1 | 1 | 0.22 | 0 | 2 | 50.0 | 300.0 | | 100.0 | | 40.00 |
| 2 | 2 | 2 | 0.33 | 0 | 2 | 40.0 | 40.0 | | 230.0 | | 35.00 |
| 3 | 1 | 3 | 0.10 | 0.00 | 2 | 50.0 | 30 | | 40.0 | 3.00 | 20.00 |
| 4 | 3 | 4 | 0.40 | 0.25 | 6 | 45.0 | 105.0 | 55.0 | 70.0 | 20.00 | 40.00 |
| | | 5 | 0.40 | 0.40 | 4 | 45.0 | 250.0 | 12 | 15 | 30 | 10 |
| | | 6 | 0.15 | 0.10 | 3 | 40.0 | 30 | | 45 | 35 0 | 10 |

*The number of observers and measurements for a single observer

What is claimed is:

1. An industrial viewing station for inspection of defects in a vehicle surface to be examined; said industrial viewing station comprising:
   a) a visual surround defining an interior sized to receive at least a portion of the vehicle;
      i) said visual surround covering the interior in order to selectively control entry of outside light into the interior and to selectively control internal luminance;
   b) a lighting arrangement having: a first selected lighting condition and a second selected lighting condition;
      i) said first selected lighting condition comprising directional lighting selectively oriented to direct light at the surface to be examined;
      ii) said second selected lighting condition comprising surround illuminating light selectively oriented to illuminate the visual surround; and
   c) a control system for selectively activating said first selected lighting condition and said second selected lighting condition.

2. An arrangement according to claim 1 further comprising:
   a) a pattern system constructed and arranged for viewing a selected pattern reflected by the surface to be viewed.

3. An arrangement according to claim 1 wherein the control system automatically configures said lighting conditions according to vehicle finish characteristics.

4. An arrangement according to claim 1 wherein:
   a) said first selected lighting condition comprising lighting selected in accordance with a first viewer's viewing preferences and visual performance; and
   b) said second selected lighting condition comprising lighting selected in accordance with a second viewer's viewing preferences and visual performance.

5. An arrangement according to claim 1 wherein:
   a) said first selected lighting condition is configured for viewing a surface of a first color:
      i) said first selected lighting condition including surround illuminating light of a first low level; and
   b) said second selected lighting condition is configured for viewing a surface of a second color lighter than said first color:
      i) said second selected lighting condition including surround illuminating light of a second high level, higher than said first low level.

6. An arrangement according to claim 1 wherein:
   a) said first and said second selected lighting conditions comprising at least one lighting source selected from the group consisting of:
      i) point source lighting selectively orientable generally perpendicular to the surface to be examined;
      ii) linear source lighting selectively orientable generally vertically; and
      iii) area source lighting selectively orientable to provide generally uniform luminance of an area in which the vehicle is positioned for examination.

7. An arrangement according to claim 6 wherein:
   a) said point source lighting comprises at least one light source selected from the group consisting of:
      i) incandescent lighting;
      ii) quartz-halogen lighting;
      iii) high intensity discharge lighting;
      iv) fluorescent lighting;
      v) sulfur lighting;
      vi) low voltage lighting; and
      vii) fiber optic lighting.

8. An arrangement according to claim 6 wherein:
   a) said linear source lighting comprises at least one light source selected from the group consisting of:
      i) high intensity discharge;
      ii) fluorescent lighting;
      iii) neon lighting;
      iv) fiberoptic lighting; and
      v) tubular lighting.

9. An arrangement according to claim 6 wherein:
   a) said area source lighting comprises at least one light source selected from the group consisting of:
      i) a luminous panel;
      ii) a reflected panel;
      iii) a back lit panel;
      iv) a projection system; and
      v) a flat screen.

10. An arrangement according to claim 1 wherein:
    a) the inspection is made by a human being.

11. An arrangement according to claim 1 wherein:
    a) the inspection is made by a machine vision system.

12. An arrangement according to claim 1 wherein:
    a) objective visibility measurements are measured by a machine vision system;
    b) said machine vision system comprising:
       i) a video camera connected to a computer system, said computer system being programmed with scene imaging capture and calculation software, said computer system having a defect database containing visibility measurements representative of samples having defects and no defects; and
    c) said machine vision system compares the detected visibility measurements to the defect database to determine if the objective visibility measurements contain a defect.

13. An inspection lighting system for inspection of defects in a vehicle surface to be examined; said inspection lighting system comprising:
    a) a visual background against which the surface to be examined is selectively examined;
    b) a lighting arrangement having: a first selected lighting condition; and, a second selected lighting condition;
    c) said first and second selected lighting conditions comprising:
       i) point source lighting selectively orientable generally perpendicular to the surface to be inspected;
       ii) linear source lighting selectively orientable generally vertically;
       iii) area source lighting selectively orientable to provide generally uniform luminance of an area in which the vehicle is positioned for examination; and
    d) a control system for selectively controlling said first selected lighting condition and said second selected lighting condition.

14. An arrangement according to claim 13 further comprising:
    a) a pattern system construed and arranged for viewing a selected pattern reflected by the surface to be viewed.

15. An arrangement according to claim 13 wherein the control system automatically configures said lighting conditions according to vehicle finish characteristics.

16. An arrangement according to claim 13 wherein:
    a) said first selected lighting condition comprises lighting selected in accordance with a first viewer's viewing preferences and visual performance; and b) said second selected lighting condition comprises lighting selected in accordance with a second viewer's viewing preferences and visual performance.

17. An arrangement according to claim 13 wherein:
a) said point source lighting comprises at least one light source selected from the group consisting of:
   i) incandescent lighting;
   ii) quartz-halogen lighting;
   iii) high intensity discharge lighting;
   iv) fluorescent lighting;
   v) sulfur lighting;
   vi) low voltage lighting; and
   vii) fiber optic lighting.

18. An arrangement according to claim 13 wherein:
a) said linear source lighting comprises at least one light source selected from the group consisting of:
   i) high intensity discharge lighting;
   ii) fluorescent lighting;
   iii) neon lighting;
   iv) fiberoptic lighting; and
   v) tubular lighting.

19. An arrangement according to claim 13 wherein:
a) said area source lighting comprises at least one light source selected from the group consisting of:
   i) a luminous panel;
   ii) a reflected panel;
   iii) a back lit panel;
   iv) a projection system; and
   v) a flat screen.

20. An arrangement according to claim 13 wherein:
a) said visual background is constructed and arranged to provide a background to at least a side of an automobile.

21. An arrangement according to claim 13 wherein:
a) the inspection lighting system is a moveable system for moving around the vehicle to be examined.

* * * * *

UNITED STATES PATENT AND TRADEMARK OFFICE
CERTIFICATE OF CORRECTION

PATENT NO.    : 5,841,530
DATED         : November 24, 1998
INVENTOR(S)   : Hewitt et al.

It is certified that error appears in the above-identified patent and that said Letters Patent is hereby corrected as shown below:

Column 1,
Line 5, change "5,686,915" to -- 5,686,987 --.

Column 4,
Line 50, delete "the" after "of".

Column 17,
Line 6, "Identification of Preferred Viewing Conditions" should be a heading and also a new paragraph.

Column 20,
Line 9, "The" should not start a new paragraph.

Column 22,
Line 30, change ".3" to -- 103. --.

Column 23,
Line 16, change "be" to -- being --.

Column 24,
Line 7, change "Lest" to -- test --.

Column 28,
Line 65, delete "("after "only".

Column 29,
Line 39, delete "20" after "the".

Column 30,
Line 41, change "laboratory measurements" to -- Laboratory Measurements --.

Column 31,
Line 14, change "addition" to -- additional --.

UNITED STATES PATENT AND TRADEMARK OFFICE
CERTIFICATE OF CORRECTION

PATENT NO.     : 5,841,530
DATED          : November 24, 1998
INVENTOR(S)    : Hewitt et al.

It is certified that error appears in the above-identified patent and that said Letters Patent is hereby corrected as shown below:

Column 32,
Line 26, delete "35" after "having".

Signed and Sealed this

Thirteenth day of November, 2001

Attest:

*Nicholas P. Godici*

NICHOLAS P. GODICI
*Attesting Officer*     *Acting Director of the United States Patent and Trademark Office*

UNITED STATES PATENT AND TRADEMARK OFFICE
CERTIFICATE OF CORRECTION

PATENT NO.   : 5,841,530
DATED        : November 24, 1998
INVENTOR(S)  : Hewitt et al.

It is certified that error appears in the above-identified patent and that said Letters Patent is hereby corrected as shown below:

<u>Title page,</u>
Insert item [73] as -- [73] Assignee: Orfield Associates, Inc., Minneapolis, MN --.

Signed and Sealed this

First Day of April, 2003

JAMES E. ROGAN
*Director of the United States Patent and Trademark Office*